(12) United States Patent
Woodard, Jr. et al.

(10) Patent No.: US 6,676,641 B2
(45) Date of Patent: Jan. 13, 2004

(54) RETRACTABLE HYPODERMIC SYRINGE

(75) Inventors: James A. Woodard, Jr., Powell, OH (US); J Douglas Dickson, Columbus, OH (US); Brian R. Fortner, New Albany, OH (US)

(73) Assignee: Futura Medical Technologies, Inc., Solano Beach, CA (US)

( * ) Notice: Subject to any disclaimer, the term of this patent is extended or adjusted under 35 U.S.C. 154(b) by 13 days.

(21) Appl. No.: 09/948,061

(22) Filed: Sep. 5, 2001

(65) Prior Publication Data

US 2003/0045838 A1 Mar. 6, 2003

(51) Int. Cl.$^7$ ................................................ A61M 5/00
(52) U.S. Cl. ......................................................... 604/187
(58) Field of Search ................................ 604/110, 187, 604/196, 506, 121, 124, 125, 131, 181, 188

(56) References Cited

U.S. PATENT DOCUMENTS 5,891,105 A * 4/1999 Mahurkar .................. 604/195
6,464,183 B1 * 10/2002 Bouhuijs .................... 248/118

* cited by examiner

Primary Examiner—Manuel Mendez
Assistant Examiner—Kevin C. Sirmons
(74) Attorney, Agent, or Firm—Fulbright & Jaworski L.L.P.

(57) ABSTRACT

A hypodermic syringe includes a barrel with a plunger assembly slidably extending therein. The plunger assembly includes an outer plunger and an inner plunger telescoping together with a bungee resisting extension of the assembly. The inner and outer plungers may be locked in the extended position with the bungee in tension. A seal stop is located at the seal end of the plunger assembly and holds an annular seal in radial extension sealing against the internal sidewall of the barrel. A luer hub assembly is fixed at the needle end of the barrel. A plunger cap may be advanced after injection to rotate the plunger assembly. Such rotation engages a probe on the end of the plunger assembly with the luer hub, disengages the seal stop to release the annular seal, engages the seal stop with the luer plunger assembly causing release of the luer hub assembly from the barrel and releases the engagement between the outer plunger and inner plunger. The foregoing provides for the retraction of the luer hub and associated needle into the barrel.

73 Claims, 26 Drawing Sheets

RETRACTABLE HYPODERMIC SYRINGE

BACKGROUND OF THE INVENTION

The field of the present invention is hypodermic syringes with safety systems for the avoidance of sharps injuries.

For some time the art has recognized the desirability of protecting personnel from accidental sharps injuries, or needle sticks, and against contact with fluid that leaks, drips or is sprayed from a syringe after the syringe is used to deliver an injection. Sometimes, after a syringe is used to inject fluid into a patient, some fluid remains in the syringe, particularly at the tip of the needle. This fluid may include the fluid injected into the patient from the syringe and/or body fluids from the patient such as blood. Any fluid remaining in the syringe after use of the syringe may leave the syringe, such as by leaking, spraying or dripping from the syringe and may contact persons or objects in the area. Syringes with retractable needles may be especially prone to this loss of fluid when the needle quickly retracts into the barrel of the syringe after injection.

More recently, concerns have been expressed about the possibility of transmitting serious or potentially fatal infections as a result of sharps accidents. Most recently, legislation requiring the use of safe needle technology is pending in a number of states and before the Occupation Safety and Health Administration. Safe, conveniently used and inexpensive systems are needed which reduce the amount of manual manipulation required to make the needle safe against sharps injuries and fluid dispersal.

SUMMARY OF THE INVENTION

The present invention is directed to apparatus and methods of operation for hypodermic syringe systems with retractable needles. The syringe includes a barrel and a plunger assembly slidably extending into the barrel with features and steps permitting further manipulation of the plunger following injection to retract a luer hub assembly and needle into the barrel.

In a first separate aspect of the present invention, the plunger assembly includes a hollow outer plunger assembly, a hollow inner plunger assembly and a resilient tension element extending between the two assemblies which is just substantially relaxed with the outer and inner plunger assemblies telescoped together. A releasable engagement between the outer and inner plunger assemblies is able to retain the assemblies telescoped to an extended position. Thus, a collapsible plunger is provided.

In a second separate aspect of the present invention, the first separate aspect may be further contemplated to include a socket on the outer plunger assembly and a resiliently mounted pin on the inner plunger assembly which engage with the plunger assemblies telescoped to an extended position. The barrel of the syringe may include a release element to engage the releasable engagement through manipulation of the plunger. Such manipulation may include extra force or torque on the plunger thumb button. Avoidance of required manipulation with the other hand or adjacent the needle can be avoided.

In a third separate aspect of the present invention, the first separate aspect is further contemplated to include indexing between the inner and outer plunger assemblies, a stop between the barrel at the plunger opening and the inner plunger assembly at its locking end and selective indexing between the overall plunger assembly and the barrel. Such constraints on the plunger assemblies enables operation of the system with minimal operator manipulation.

In a fourth separate aspect of the present invention, the plunger assembly includes a plunger and a cap at one end of the plunger. The cap has a cylindrical wall with a helical cam surface and a track extending longitudinally of the plunder assembly. The plunger includes a resiliently mounted lock that retains the cap and the plunger from rotating relative to one another. The resiliently mounted lock includes a disengagement ramp. The barrel includes an internal rail which is able to interfere with the resiliently mounted lock at the disengagement ramp to displace the lock from the track upon near full insertion of the plunger in the barrel. This displacement is able to fix the cap from rotating relative to the barrel and release the plunger to rotate relative to the cap. As such, the helical cam surface is able to interact with a follower pin on the plunger to rotate the plunger relative to the barrel while the cap remains from rotating relative to the barrel. In this way, rotation may be selectively employed to actuate the syringe retraction mechanism and otherwise the plunger remains indexed relative to the barrel during charging and injecting operations.

In a fifth separate aspect of the present invention, the plunger includes a probe extending from the seal end of the plunger. A seal stop is positioned about the probe and is held thereto by an axially releasable engagement between the probe and the stop. An annular seal is positioned between the plunger at the seal end and the seal stop. The seal is found to be in sealed engagement with the internal sidewall of the barrel with the seal stop in mated engagement with the plunger and in disengagement with the internal sidewall when the seal stop is disengaged from the plunger. The ability to reduce seal friction between the plunger and the barrel for needle retraction can thus be achieved.

In a sixth separate aspect of the present invention, the plunger assembly includes a probe at the seal end with a retainer lug on the probe. A luer hub assembly is positioned in the barrel with a body having a needle end, an engagement end, a means to retain a needle and a retainer surface which faces the body near the engagement end and is engagable with the retainer lug through rotation of the plunger. The plunger may thus be coupled with the entire luer hub assembly for further manipulation. The retainer surface and the retainer lug may be axially displaced from one another with the plunger assembly fully extended into the barrel even though the retainer lug is aligned in engagement with the retainer surface. The spacing is able to allow for a short retraction of the plunger prior to drawing on the luer hub assembly. This retraction is capable of being employed to void an associated needle of fluid.

In a seventh separate aspect of the present invention, the plunger assembly includes a probe extending axially from the seal end of the plunger. A seal stop is positioned about the probe. An axially releasable engagement enables the seal stop to be retained in mated relationship with the seal end of the plunger as well as axially released therefrom. The seal stop provides a vehicle for accomplishing functions advantageous for luer hub and needle retraction.

In an eighth separate aspect of the present invention, the seventh separate aspect is contemplated to further include a portion inwardly tapered on the internal sidewall of the barrel to cooperate with a seal about the luer hub assembly. Extraction of the luer hub assembly through the barrel can operate through the taper to gradually release the seal about the body of the luer hub assembly, reducing initial acceleration imposed on a retracting needle. Reduced acceleration can limit the amount of liquid separated from the needle during retraction.

In a ninth separate aspect of the present invention, a seal stop is associated with the seal end of the plunger assembly. The seal stop includes an inwardly facing cam surface facing a luer hub assembly which includes a latch pin engagable with an internal stop and having a cam follower engagable with the inwardly facing cam surface. The releasable seal stop is thus able to actuate the latch pin to release the luer hub assembly within the barrel from the internal stop.

In a tenth separate aspect of the present invention, the ninth separate aspect is contemplated to further include mutually engaging surfaces between the seal stop and the luer hub assembly able to draw the seal stop and the luer hub assembly toward one another to actuate the resiliently mounted latch pin. In this way, the seal stop releasably engaged with the seal end of the plunger can be released to become engaged with the luer hub assembly for release of the luer hub assembly from the barrel.

In an eleventh separate aspect of the present invention, a hypodermic syringe retraction method includes extending the plunger assembly and a resilient tension element within the barrel of the syringe where the plunger assembly includes an outer plunger and an inner plunger telescoped together. The outer plunger is drawn outwardly from the barrel to engage an engagement between the outer and inner plungers. The engagement between the outer and inner plungers is later released.

In a twelfth separate aspect of the present invention, the eleventh separate aspect of the present invention is further contemplated to include engaging the luer hub assembly with the plunger assembly by rotating a retainer log of the plunger assembly into spaced engagement with a retainer surface on the luer hub assembly.

In a thirteenth separate aspect of the present invention, the eleventh and twelfth separate aspects of the present invention are further contemplated to include axial pushing of a plunger cap and translating the actual push to rotation of the plunger assembly.

In a fourteenth separate aspect of the present invention, a seal stop releasably engaged on the seal end of the plunger is released to radially retract an annular seal held between the seal end of the plunger and the seal stop. The seal stop is also engaged with a luer hub assembly and the luer hub assembly is released from the barrel. With the annular seal retracted and the luer hub released, extraction of the luer hub from the end of the barrel is possible.

In a fifteenth separate aspect of the present invention, a seal stop is released from the seal end of the plunger which allows for radial retraction of a seal associated therewith. The seal stop is engaged with a luer hub assembly and drawn thereto through rotation of the seal stop. The drawing of the seal stop toward the luer hub assembly releases a latch pin engaged with the interior of the barrel. The transfer of engagement of the seal stop from the plunger assembly to the luer hub assembly thus effects multiple changes resulting in the retractability of the luer hub assembly through the barrel.

In a sixteenth separate aspect of the present invention, any of the foregoing separate aspects are contemplated to be employed in combination to greater advantage.

Accordingly, it is an object of the present invention to provide an improved method and apparatus for a needle retracting hypodermic syringe. Other and further objects and advantages will appear hereinafter.

DETAILED DESCRIPTION OF THE PREFERRED EMBODIMENT

Figure 1:
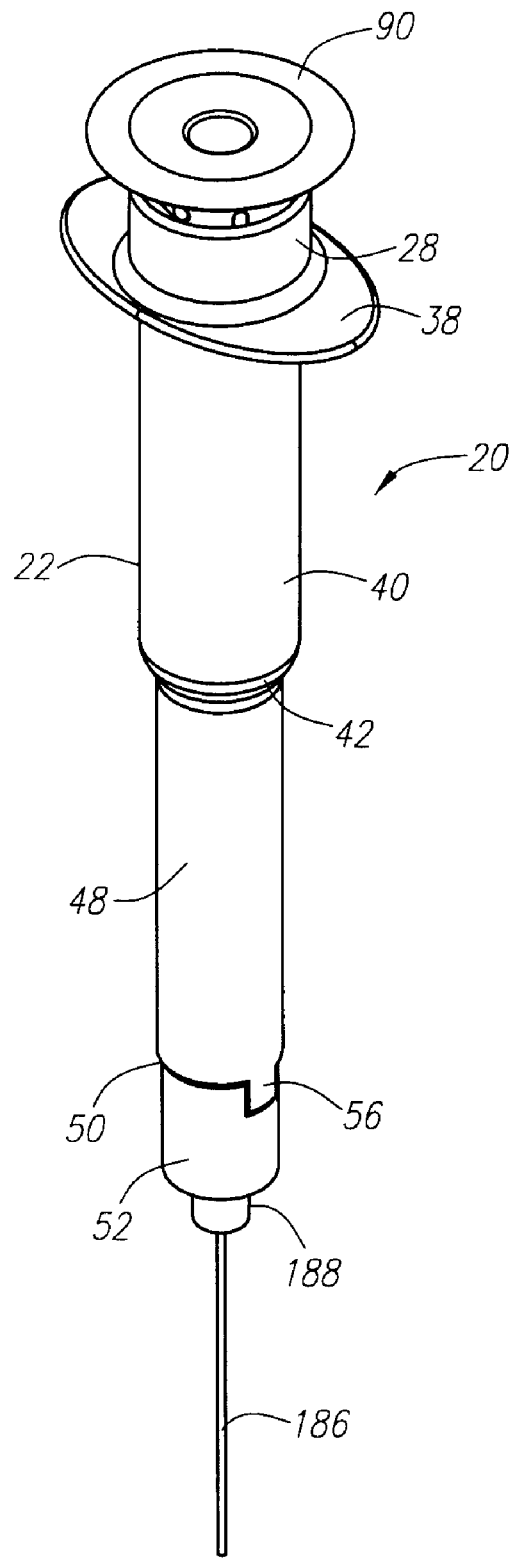
FIG. 1 is a perspective view of an assembled syringe.
Figure 2:
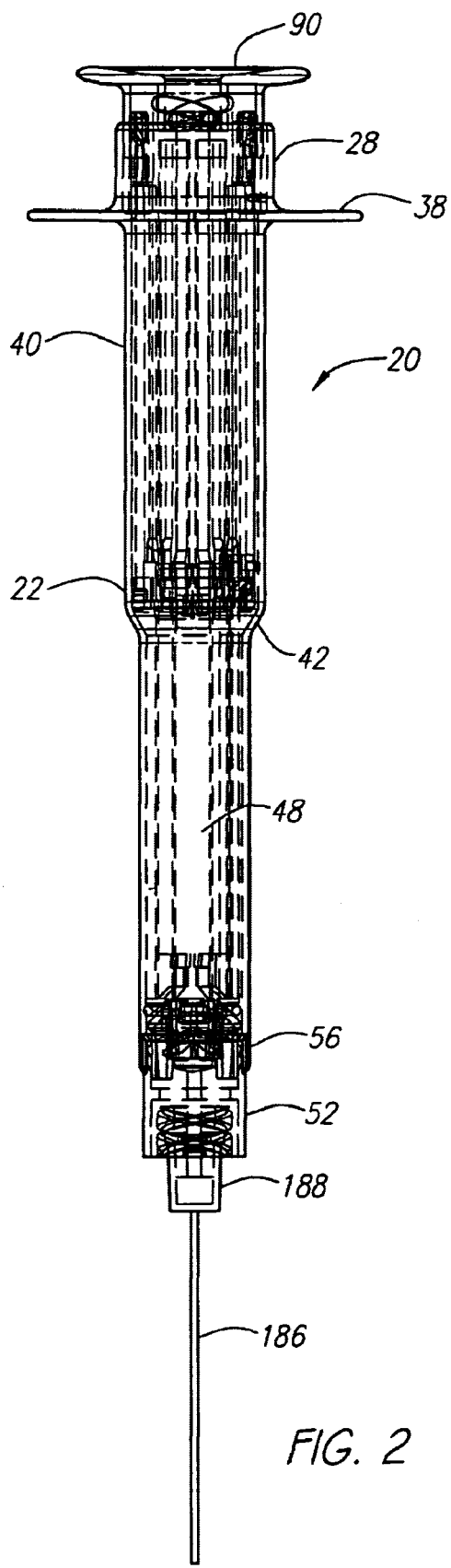
FIG. 2 is a side view of the assembled syringe.
Figure 3:
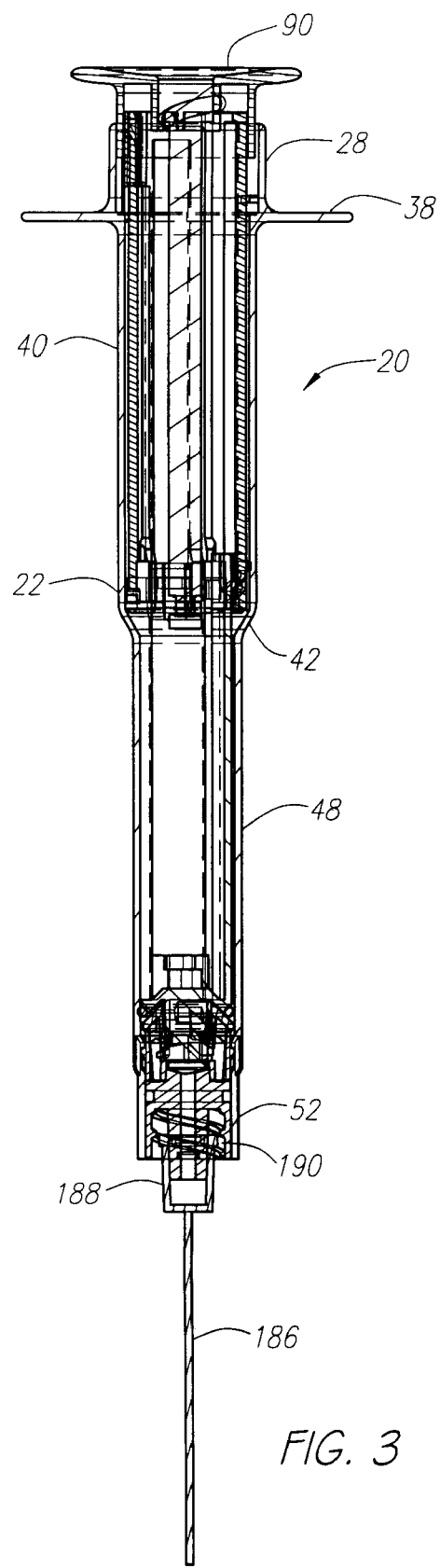
FIG. 3 is a cross-sectional view of the assembled syringe.
Figure 4:
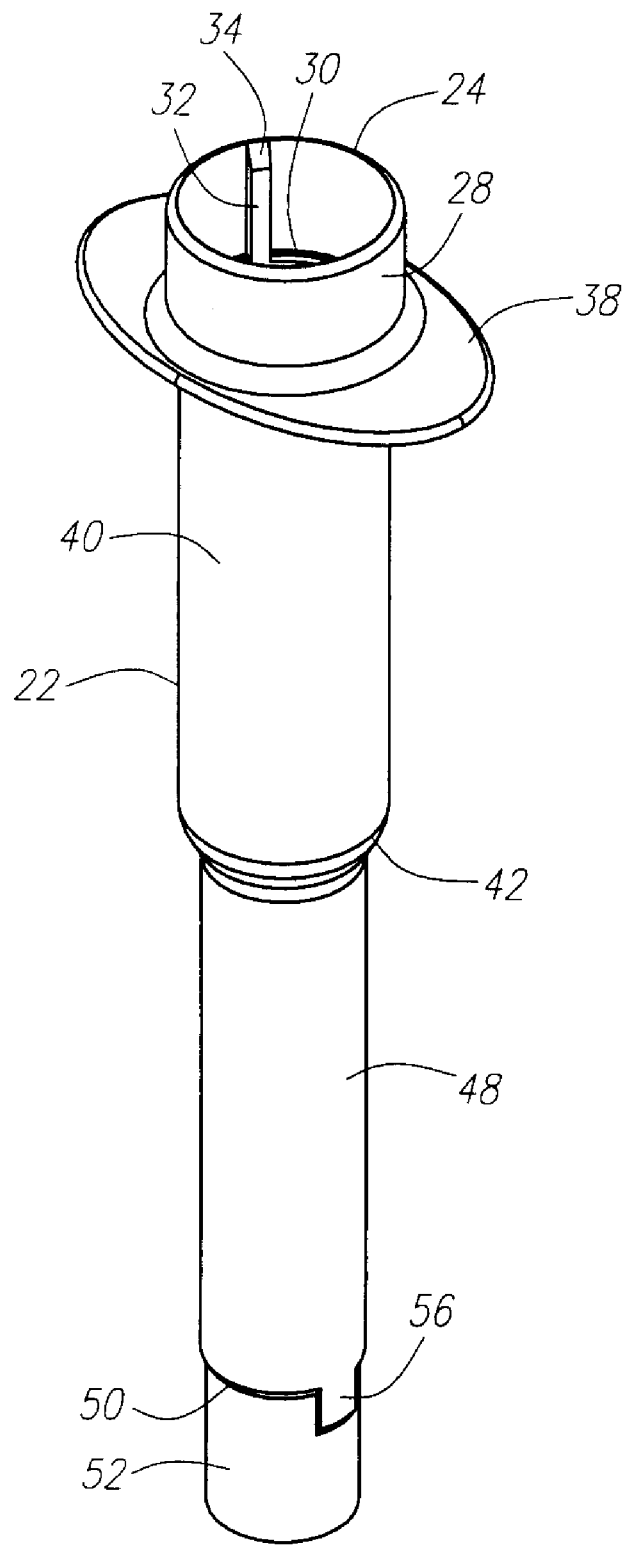
FIG. 4 is a perspective view of a syringe barrel.
Figure 5:
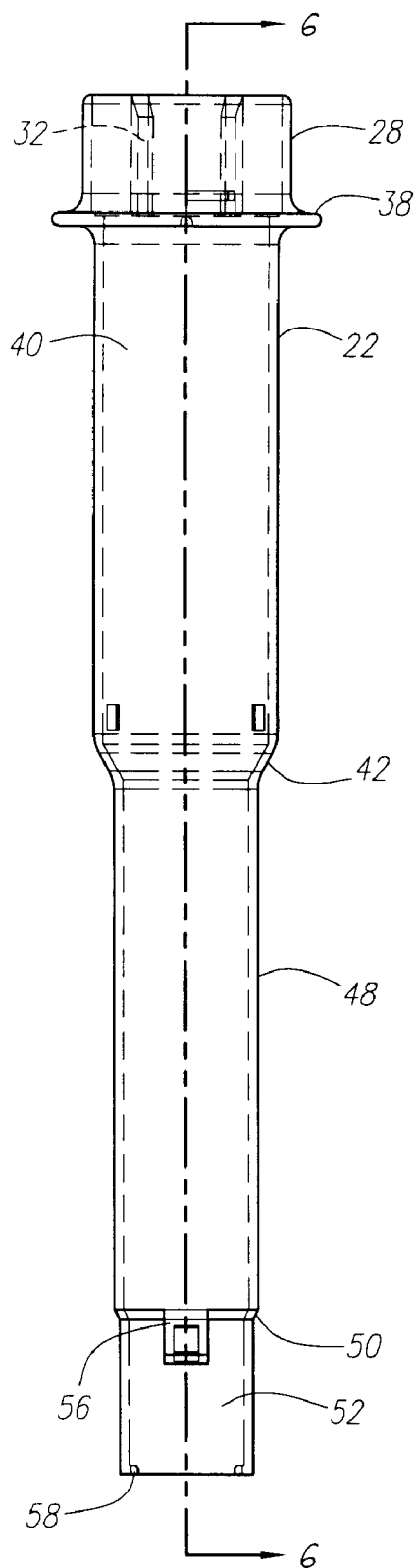
FIG. 5 is a side view of the syringe barrel.
Figure 6:
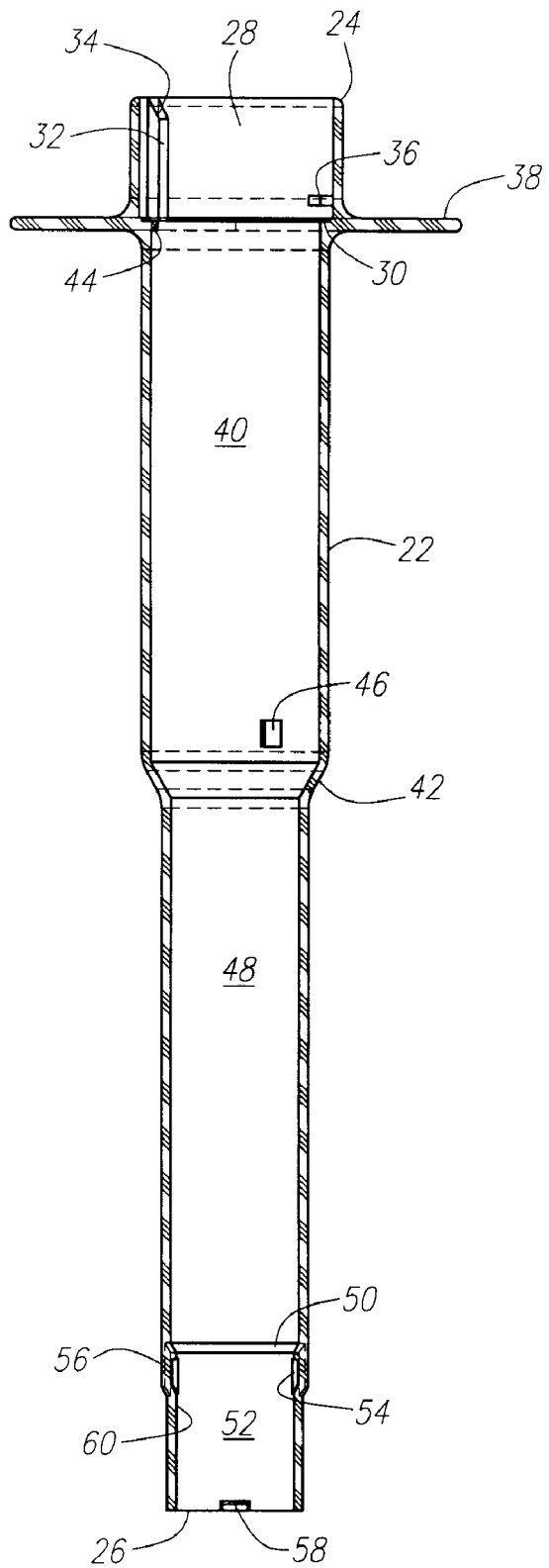
FIG. 6 is a cross section of the syringe barrel taken along line 6—6 of FIG. 5.

Turning in detail to the figures, a hypodermic syringe, generally designated 20 in FIG. 1, includes a barrel 22 having a plunger opening 24 at a first, larger end and a needle opening 26 at a second, smaller end. The barrel 22 includes an internal sidewall which may be defined in terms of hollow portions based on variations in internal diameter as separately illustrated in FIGS. 4 through 8.

A first hollow portion 28 extends from the plunger opening 24 to a first inward transition portion 30. This first portion 28 has two longitudinally extending internal rails 32. These rails extend the length of the first portion 28 with a ramp 34 at the plunger opening 24. The rails each extend inwardly only to the inner diameter of the transition portion 30 and terminate at that point. An inwardly extending plunger stop 36 is located spaced from the inward transition portion 30 in the first hollow portion 28 and extends inwardly beyond the minimum diameter of the inward transition portion 30.

A flange extending outwardly from the barrel 22 at the transition portion 30 defines a finger grip 38. The finger grip 38 may be configured and located to satisfy various ergonomic requirements.

Figure 7:
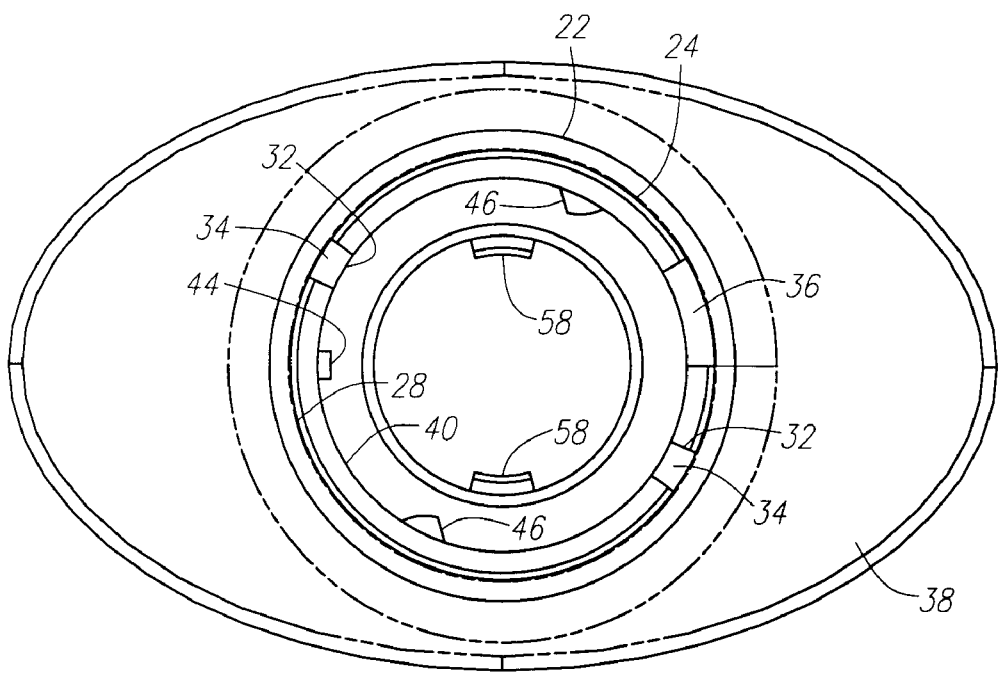
FIG. 7 is a top view of the syringe barrel.
Figure 8:
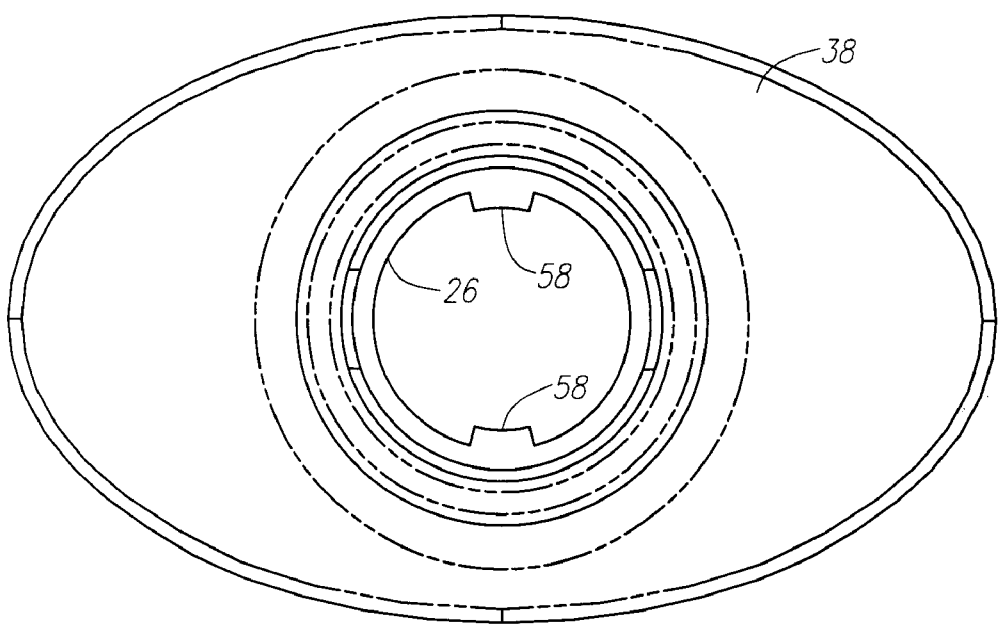
FIG. 8 is a bottom view of the syringe barrel.
Figure 9:
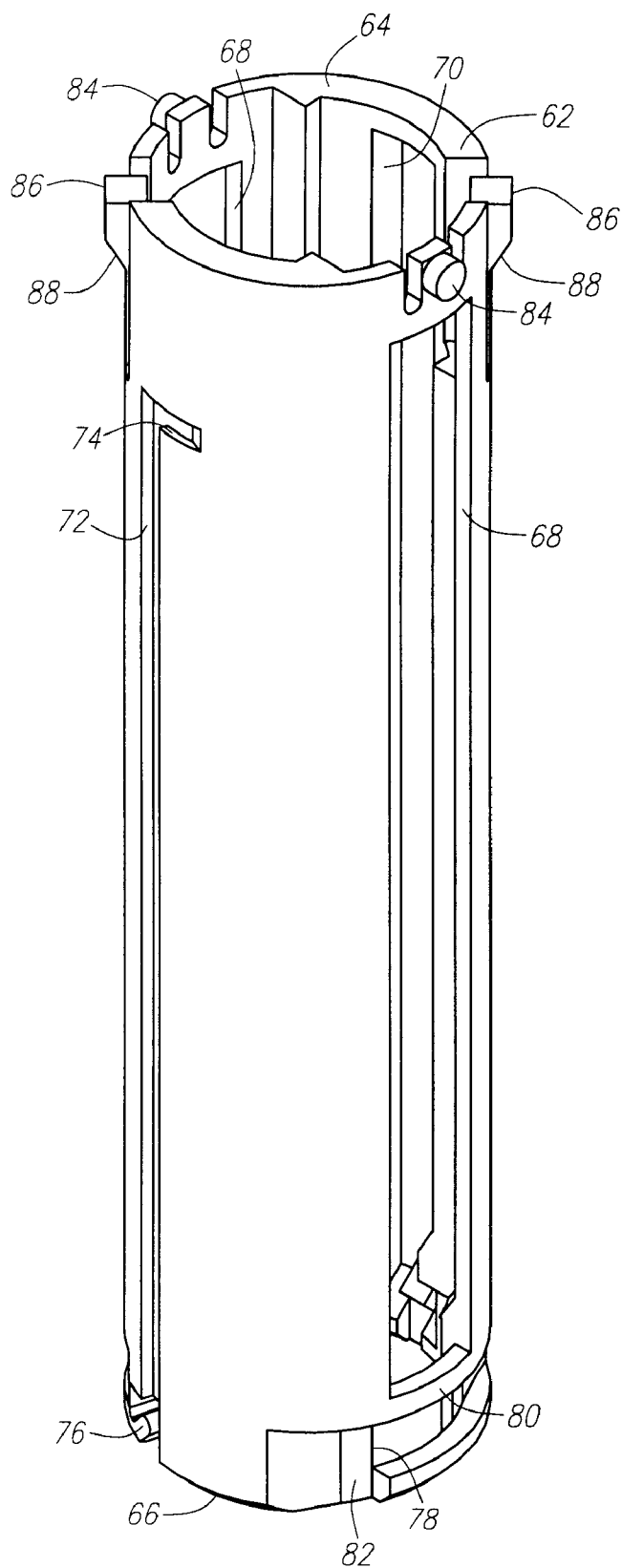
FIG. 9 is a perspective view of an outer plunger.
Figure 10:
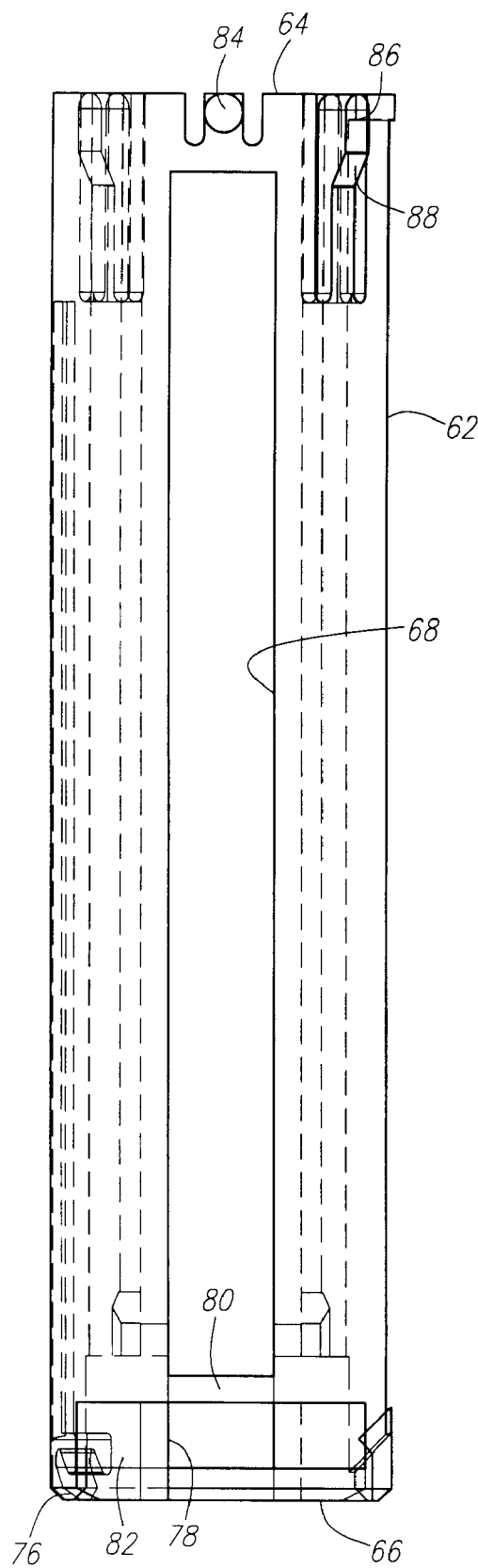
FIG. 10 is a side view of the outer plunger.
Figure 11:
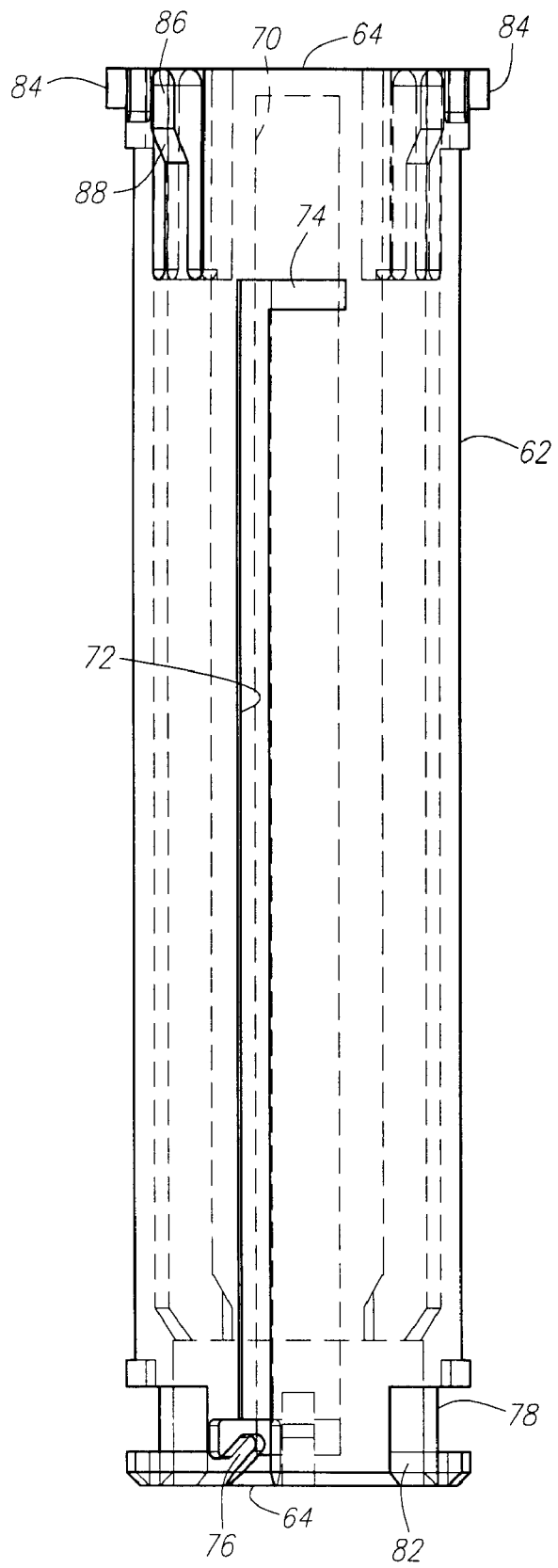
FIG. 11 is a side view of the outer plunger.
Figure 12:
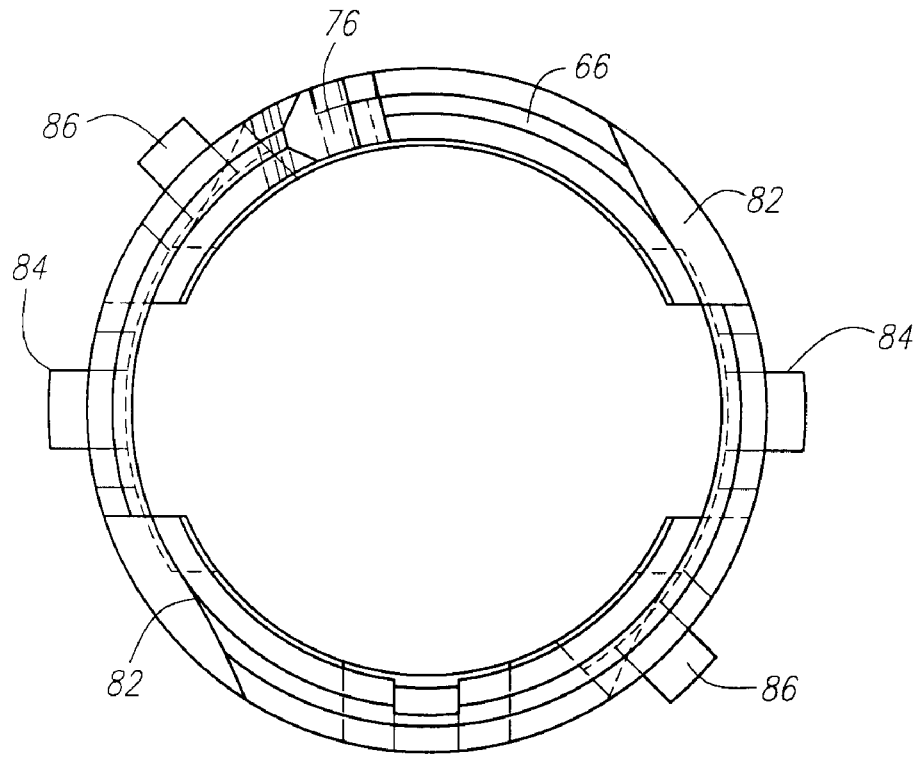
FIG. 12 is a bottom view of the outer plunger.
Figure 13:
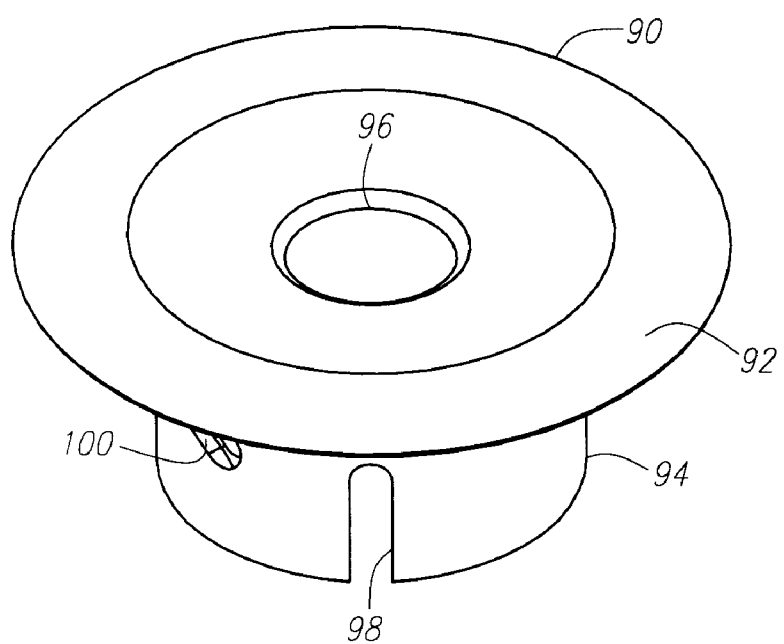
FIG. 13 is a perspective view of a plunger cap.
Figure 14:
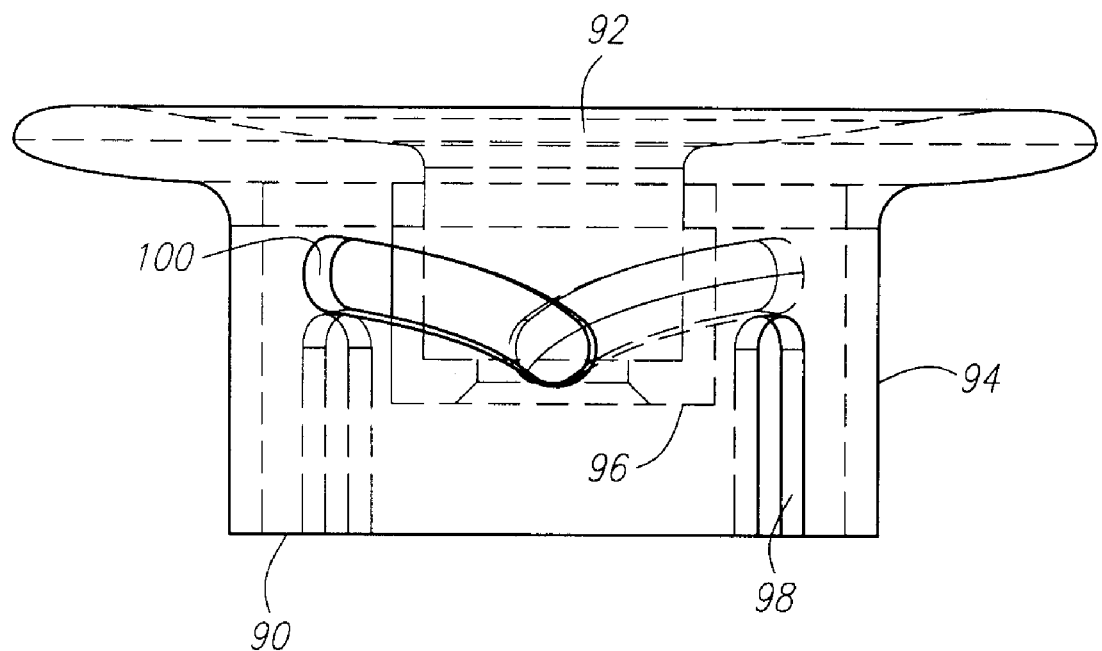
FIG. 14 is a side view of the plunger cap.
Figure 15:
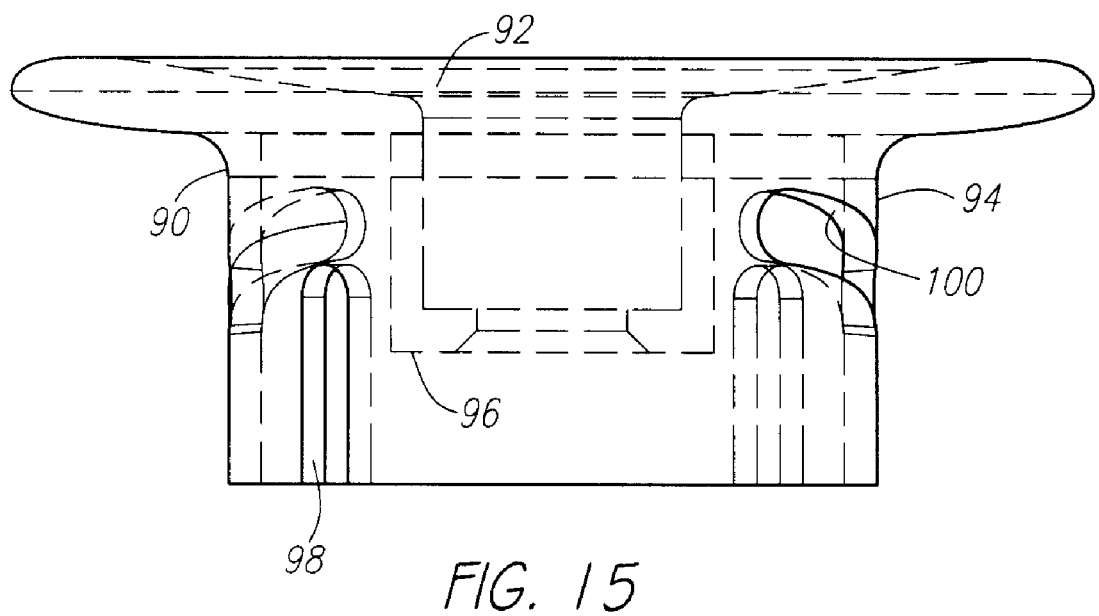
FIG. 15 is a side view of the plunger cap.
Figure 16:
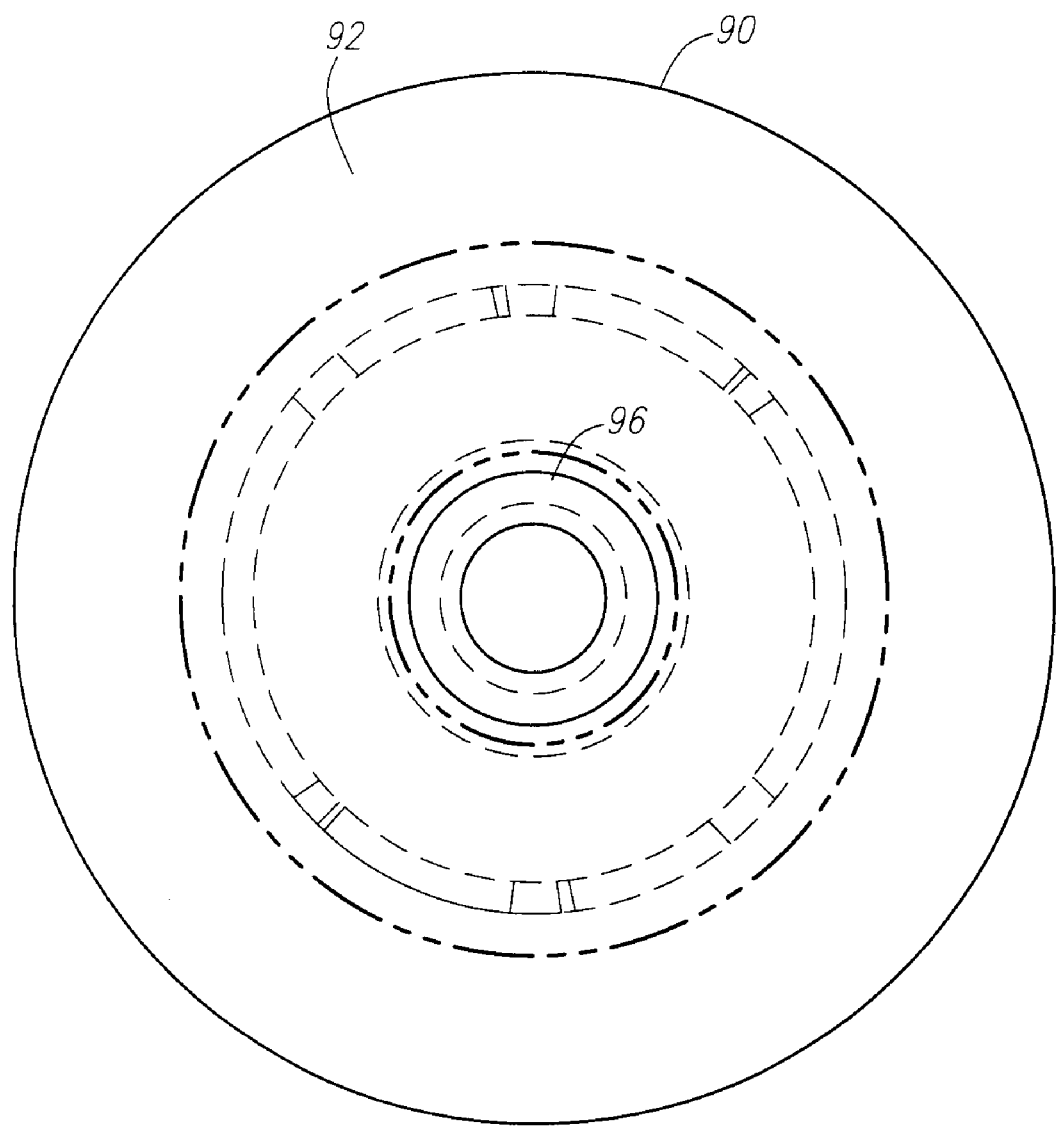
FIG. 16 is a bottom view of the plunger cap.
Figure 17:
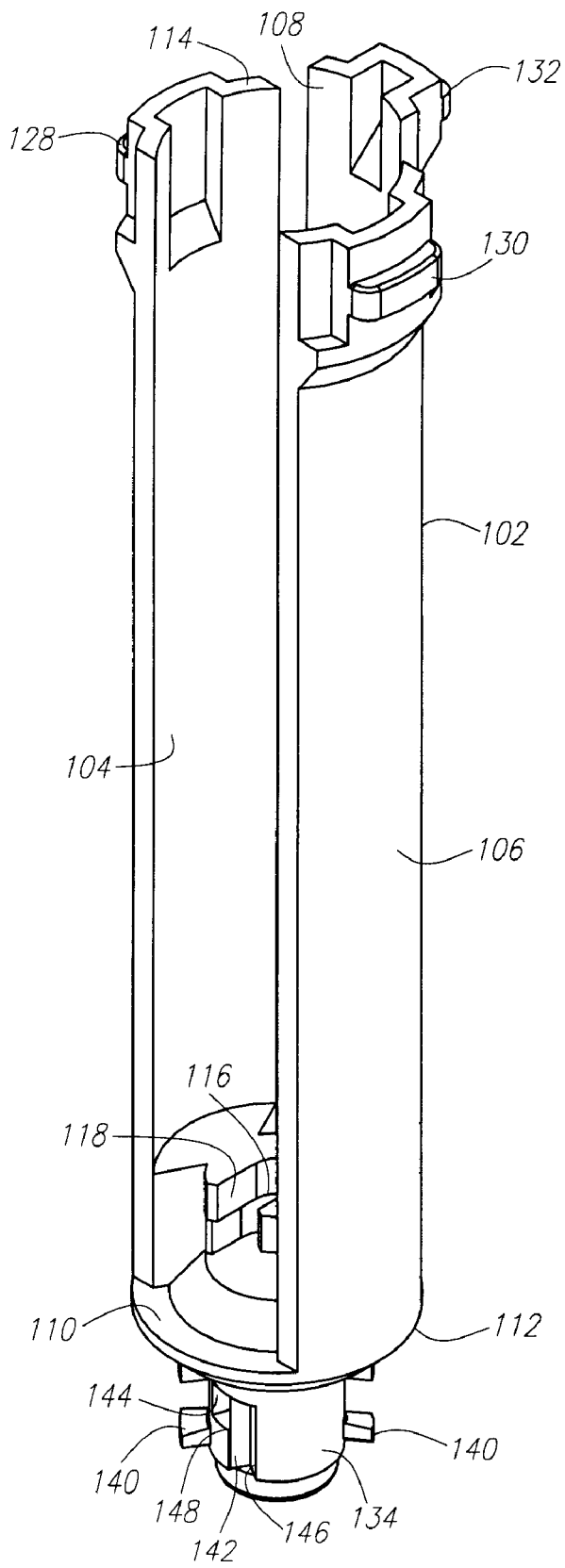
FIG. 17 is a perspective view of an inner plunger.
Figure 18:
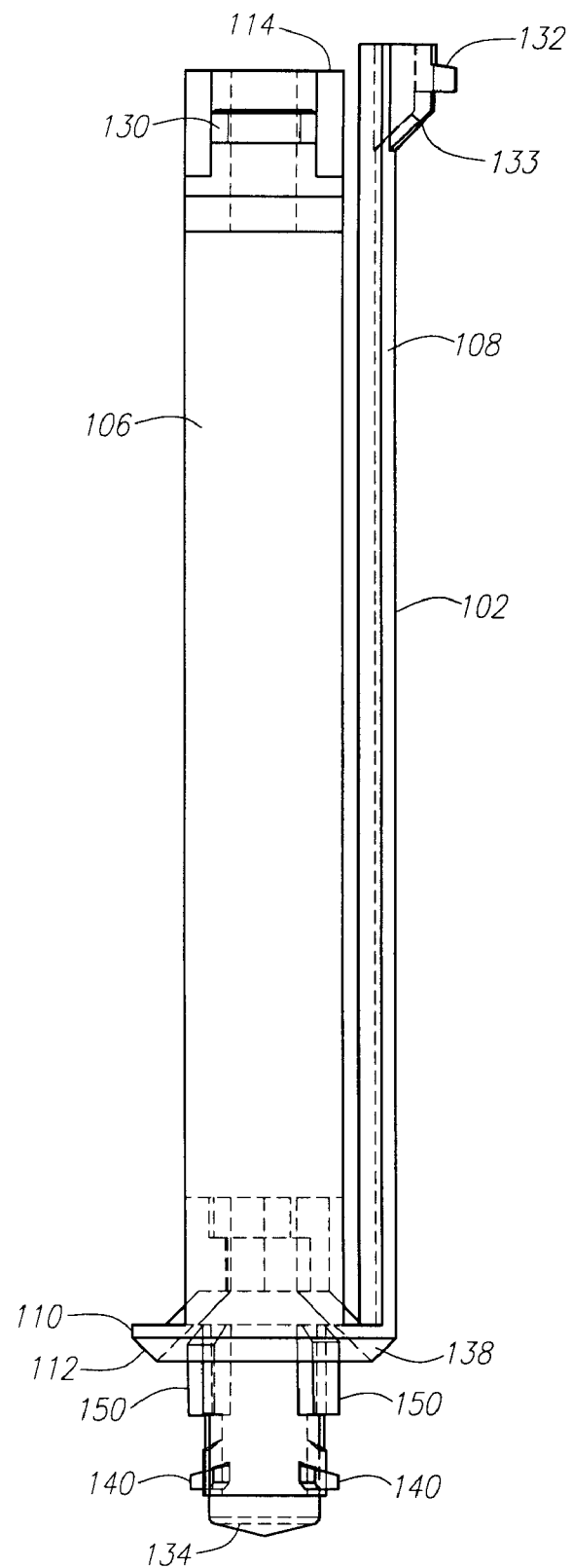
FIG. 18 is a side view of the inner plunger.
Figure 19:
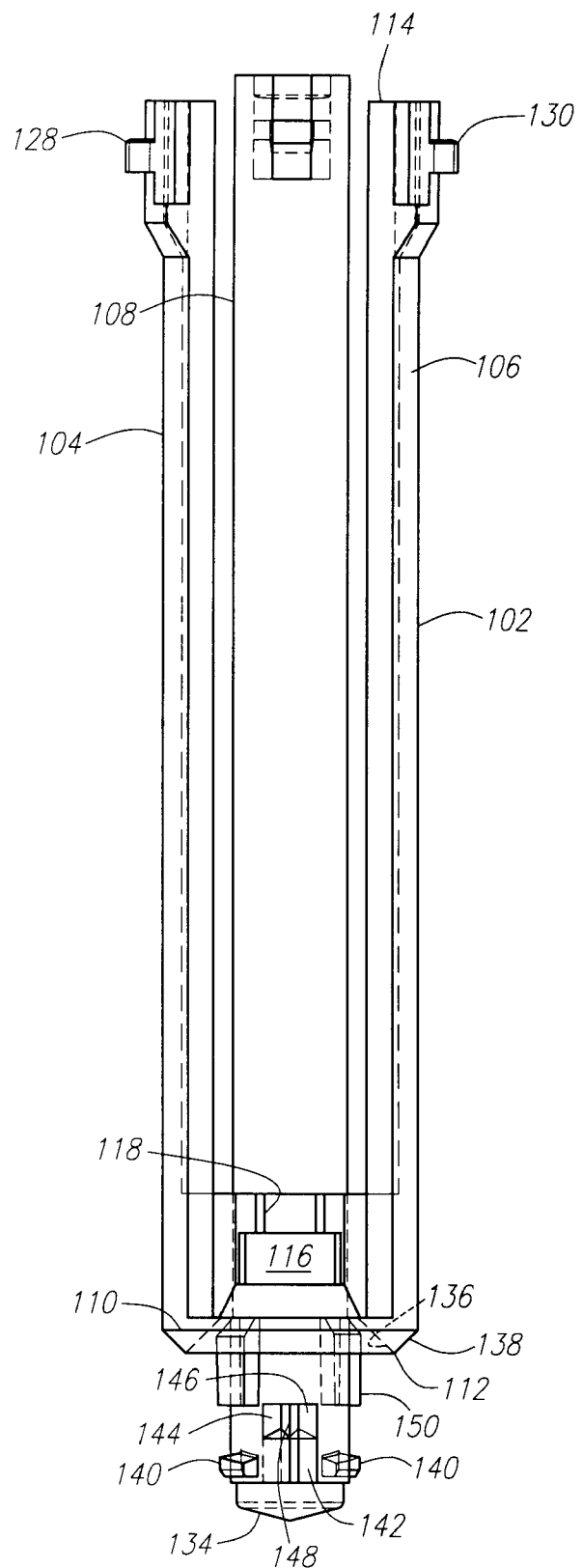
FIG. 19 is a side view of the inner plunger.
Figure 20:
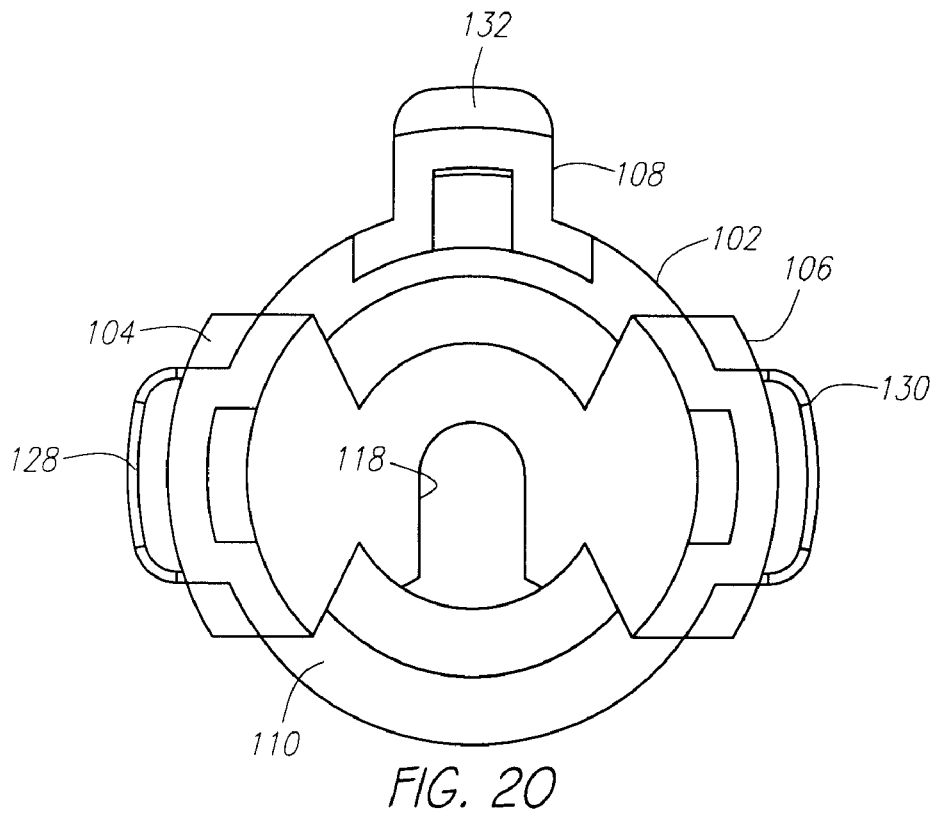
FIG. 20 is a top view of the inner plunger.
Figure 21:
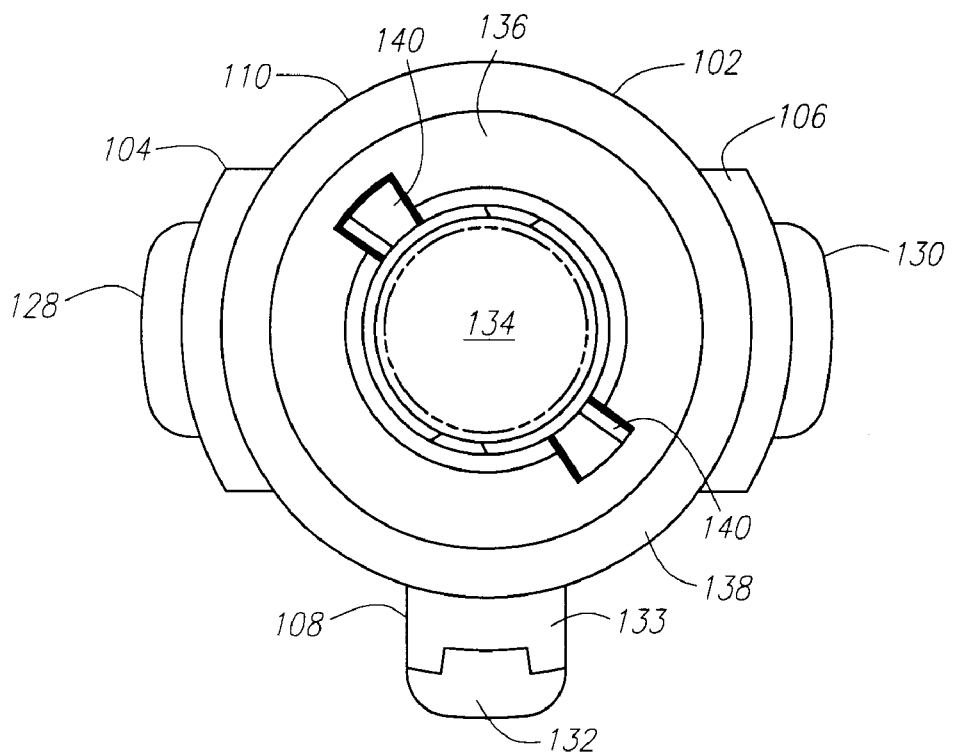
FIG. 21 is a bottom view of the inner plunger.

A second hollow portion 40 extends from the inward transition portion 30 of the first hollow portion 28 to a second inward transition portion 42. This second hollow portion 40 is shown to have a diameter which is less than the first hollow portion 28. A plunger guide 44 extends inwardly from the second hollow portion 40 immediately adjacent the first inward transition portion 30. Two release elements 46 are arranged diametrically on the interior of the hollow portion 40 near the inward transition portion 42. These release elements 46 are inwardly extending ramps as can be seen in FIG. 7.

A third hollow portion 48 of the barrel 22 extends from the inward transition portion 42. This third hollow portion 48 has an inner diameter less than that of the second hollow portion 40. This portion terminates in an inward transition portion 50. Otherwise, the interior of the hollow portion 48 is without inwardly extending elements.

A fourth hollow portion 52 extends from the inward transition portion 50 of the third hollow portion 48 to the needle opening 26. These four hollow portions 28, 40, 48 and 52 have a common centerline. The fourth hollow portion 52 includes two diametrically placed internal stops 54. These stops 54 define cavities with the edge most distant from the needle opening 26 providing a shoulder against which a luer hub assembly can be retained. The internal stops 54 are of sufficient depth that a profile 56 is shown on the outside surface of the barrel 22 for each stop to accommodate the inset. Two luer hub stops 58 diametrically positioned are located at the needle opening 26 and extend inwardly for indexing and restricting axial extraction of a luer hub assembly positioned in the fourth hollow portion 52. A portion 60 of the internal wall of the barrel 22 within the fourth hollow portion 52 is inwardly tapered toward the needle opening 26. Thus, the taper expands toward the internal stops 54 to release the seal of an O-ring positioned about a luer hub assembly located in the hollow portion 52 as it is extracted through the barrel and into the third hollow portion 38.

A plunger assembly slidably extends into the barrel 22. This plunger assembly includes a hollow outer plunger assembly which telescopes together with a hollow inner plunger assembly. The hollow outer plunger assembly includes a plunger cap and a hollow outer plunger. The hollow outer plunger 62, illustrated in FIGS. 9 through 12, includes a cap end 64 and a locking end 66. The outer plunger 62 is generally cylindrical in body with a number of engaging elements and grooves located thereabout and therethrough. The diameter of the outer plunger 62 slides easily within the second hollow portion 40.

Two diametrically arranged longitudinal guide grooves 68 extend substantially but not fully the length of the hollow outer plunger 62. A stop groove 70 also extends through the side of the outer plunger 62 at 90° to the guide grooves 68. This groove 70 extends a bit further toward the cap end 64 than the guide groves 68. A ramp 71 is located at the lower end of the stop groove 70.

A longitudinal indexing groove 72 is positioned in the quadrant of the outer plunger 62 which does not have a guide groove 68 or the stop groove 70. The indexing groove 72 does not extend fully through the wall of the outer plunger 62, unlike the guide grooves 68 and the stop groove 70. A lateral release 74 extends circumferentially from the end of the indexing groove 72 most adjacent the cap end 64 of the outer plunger 62. The indexing groove 72 receives the plunger guide 44 extending inwardly from the second hollow portion 40. The plunger guide 44 and the longitudinal indexing groove 72 cooperate to index the outer plunger 62 to prevent relative rotation between the outer plunger 62 and the barrel 22. This indexing constraint does not include the circumstance where the outer plunger 62 extends fully into the barrel 22 such that the plunger guide 44 meets the lateral release 74. The longitudinal indexing groove 72 at the locking end 66 of the outer plunger 62 includes a guide stop 76. The guide stop 76 extends laterally across the indexing groove 72 such that it has some flexibility allowing axial insertion of the outer plunger 62 into the barrel 22 with the plunger guide 44 being forced past the guide stop 76. Once captured, the plunger guide 44 constrains the outer plunger 62 from rotation relative to the barrel 22 except at the lateral release 74 and prevents extraction through interference of the guide stop 76.

Adjacent the locking end 66 of the outer plunger 62, opposed sockets 78 extend through the wall of the plunger. These sockets 78 are each displaced from the corresponding longitudinal guide grooves 68 by a catch 80. The catch 80 continues a portion of the groove to a certain depth on the inner side of the sidewall of the outer plunger 62 for indexing purposes. One end of each of the sockets 78 is open angularly about the hollow outer plunger 62 to form an entrance 82 for the release elements 46 forming an inwardly extending ramp which cooperates with the entrance 82. With the plunger assembly advanced in the barrel 22, the release elements 46 are aligned with the entrances 82 such that rotation of the plunger assembly will cause the sockets 78 to rotate to under the release elements 46.

At the cap end 64 of the outer plunger 62, follower pins 84 extend outwardly diametrically across the plunger 62. Also at the cap end 64, resiliently mounted locks 86 extend radially outwardly from the outer plunger 62. These locks 86 are mounted with axial cuts through the sidewall of the outer plunger 62 so that they may more easily be forced inwardly. The locks have disengagement ramps 88 on the ends displaced from the cap end 64 of the outer plunger 62.

The outer plunger assembly further includes a plunger cap 90 illustrated in FIGS. 13 through 16. The plunger cap 90 includes a thumb button 92 on one end and a cylindrical wall 94 depending therefrom. Centrally mounted within the cylindrical wall 94 is a first attachment 96 defining a socket with an undercut opening to retain the resilient cylindrical end of a bungee therein. The cylindrical wall 94 includes opposed tracks 98 cut axially therein. The tracks are sized and positioned to receive the resiliently mounted locks 86 with the cylindrical wall 94 of the cap 90 positioned on the outer plunger 62 at the cap end 64. The cylindrical wall further includes two diametrically opposed helical cam grooves 100 forming helical cam surfaces to receive the follower pins 84 which engage and are slidable against the helical cam surfaces. The tracks 98 will also be found to be arranged and sized to receive the longitudinally extending internal rails 32 of the hollow portion 28 of the barrel 22.

The plunger assembly further includes a hollow inner plunger assembly 102 illustrated in FIGS. 17 through 21. The body of this plunger assembly 102 is defined by three longitudinally extending arms 104, 106, 108. The three arms 104, 106, 108 extend at 90° to one another leaving one quadrant empty. The lengths of the arms 104, 106, 108 provide resilience allowing, among other things, inward movement for assembly of the inner plunger 102 with the outer plunger 62. A circular hub 110 is located at the seal end 112 of the plunger 102 while the engagement end 114 is open. The arms 104, 106, 108 extend from the circular hub 110. Inwardly of the circular hub 110, a second attachment 116 receives a second resilient cylindrical end of a bungee. This attachment 116 provides a socket which can be entered from the side with the bungee extending through an open channel 118. The first end of the bungee may be forced or molded into the first attachment 96. However, during assembly of the outer plunger 62 and the inner plunger 102, it is easier to slide the second end of the bungee laterally into a locked engagement in the attachment 116.

Figure 22:
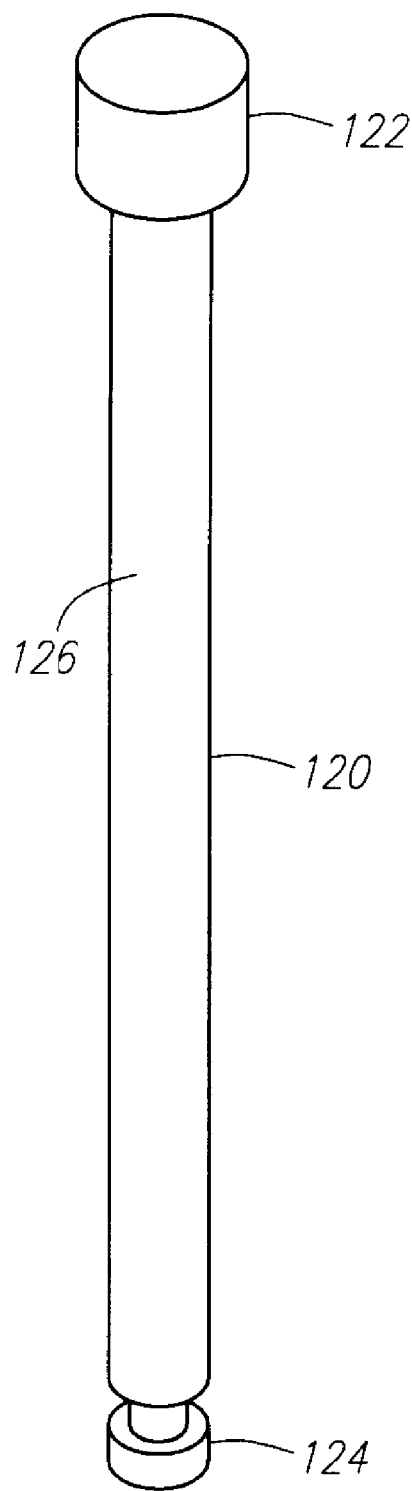
FIG. 22 is a perspective view of a resilient tension element.

A bungee 120, operating as a resilient tension element, is shown in FIG. 22 to include two resilient cylindrical ends 122, 124 providing first and second anchor shoulders with a central resilient shaft 126. Molded elastomeric material is contemplated for the bungee 120. Such materials typically yield over time when in tension. Consequently, it is appropriate to avoid tension in the resilient tension element 120 until use. With the outer plunger 62 and the inner plunger 102 assembled and telescoped together, the resilient tension element 120 is preferably just substantially relaxed such that it will not experience significant yield between the times of assembly and use. Therefore, the state of being just substantially relaxed may include minimal tension or may include a small amount of slack.

Two resiliently mounted pins 128 and 130 extend radially outwardly from the distal ends of the longitudinally extending arms 104 and 106. These two arms are identical. The pins 128, 130 engage the two longitudinal guide grooves 68 through the wall of the outer plunger 62. The cooperation of the pins 128 and 130 with the guide grooves 68 stabilize the telescoping movement of the inner plunger 102 with the outer plunger 62 and index the two plungers from rotating relative to one another. The pins 128 and 130 may each also engage and overcome a catch 80 to then spring outwardly into the opposed sockets 78. The sockets 78 along with the resiliently mounted pins 128 and 130 define a releasable engagement between the outer plunger 62 and the inner plunger 102. Once the releasable engagement is engaged, it is only released through the extension of the plunger assembly fully into the barrel 22 to align the release elements 46 with the sockets 78. Rotation of the plunger assembly causes the entrances 82 to pass over the release elements 46. The resiliently mounted pins 128 and 130 then engage the release elements 46 and are forced inwardly to such an extent that the resiliently mounted pins 128 and 130 are each free of the adjacent catch 80. As the resilient tension element 120 is extended from the just substantially relaxed state with the outer plunger 62 and the inner plunger 102 telescoped apart, the release of the resiliently mounted pins 128 and 130 allows the outer plunger 62 and the inner plunger 102 to telescope together if not otherwise constrained.

A radially extending stop 132 is resiliently mounted to the inner plunger assembly 110 by the longitudinally extending arm 108 adjacent the engagement end 114 of the inner plunger 102. This stop 132 is able to move longitudinally within the stop groove 70 and also can provide indexing to prevent rotation between the outer plunger 62 and the inner plunger 102. The radially extending stop 132 extends through this stop groove 70 and is aligned with and can engage the plunger stop 36 in the space between the plunger stop 36 and the transition portion 30. This limits the travel of the inner plunger assembly 102 so as not to exit the barrel 22. Further, the transition portion 30 prevents travel of the inner plunger 102 through the engagement of the underside of the stop 132. The stop 132 includes a release ramp 133. This ramp 133 is positioned to be engaged by the ramp 71 at the end of the stop groove 70 to release the stop pin 132 from the plunger stop 36 with the outer plunger 62 and the inner plunger 102 telescoped to an extended position.

A probe 134 extends axially from the seal end 112 of the inner plunger 102 and is attached to the circular hub 110. A cavity 136 having a truncated conical surface extends into the seal end 112 about the probe 134. Outwardly of the cavity 136, an external truncated conical surface 138 extends to the rim of the circular hub 110.

The probe 134 includes three specific engagement mechanisms. Two retainer lugs 140 extend outwardly near the distal end of the plunger 134. Bayonet slots 142 diametrically opposed are defined by a first circumferentially extending groove 144 and an axially extending groove 146. A ridge 148 reduces the depth of the bayonet slot 142 between the groove 144 and the groove 146. Consequently, some resistance to circumferential movement of a pin within the groove is intended before reaching axial release. Finally, outwardly and axially extending shoulders are defined by two diametrically opposed lugs 150 each extending about a portion of the shaft of the probe 134.

Figure 23:
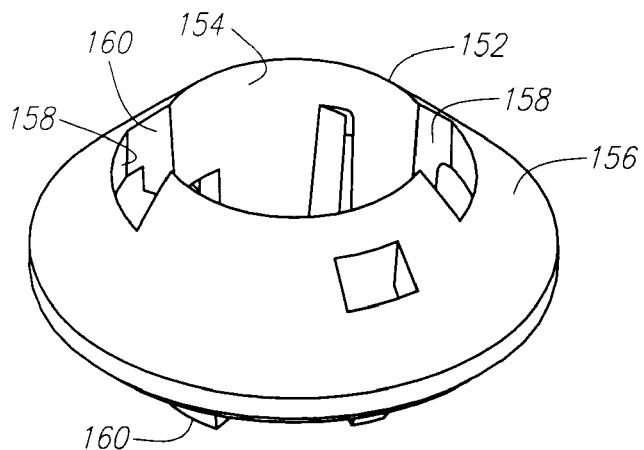
FIG. 23 is a perspective view of a seal stop.
Figure 24:
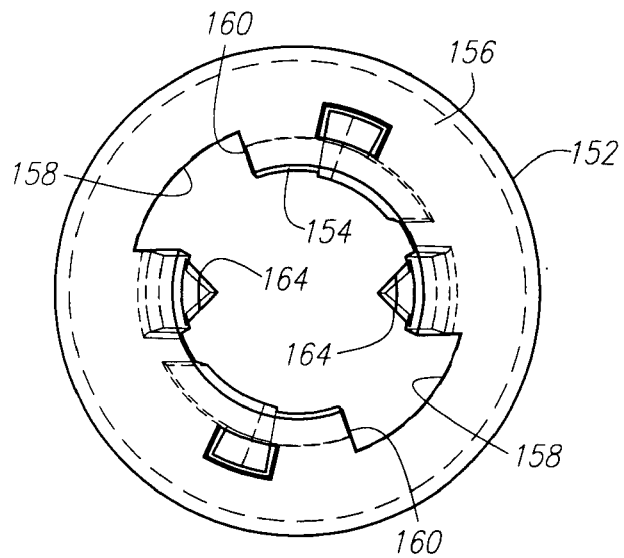
FIG. 24 is a top view of the seal stop.
Figure 25:
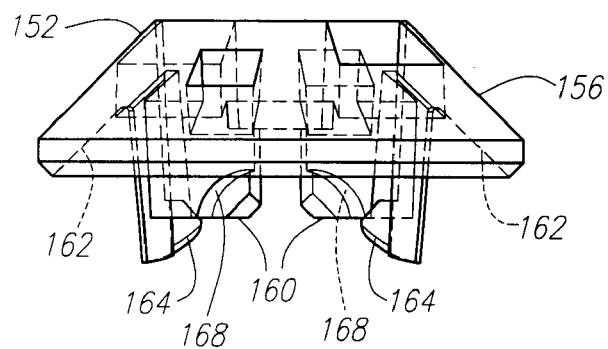
FIG. 25 is a side view of the seal stop.
Figure 26:
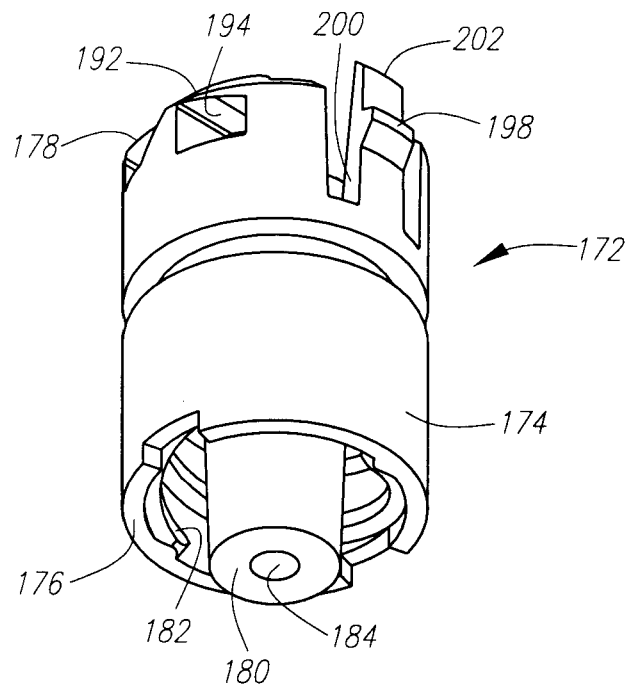
FIG. 26 is a perspective view of a luer hub assembly.
Figure 27:
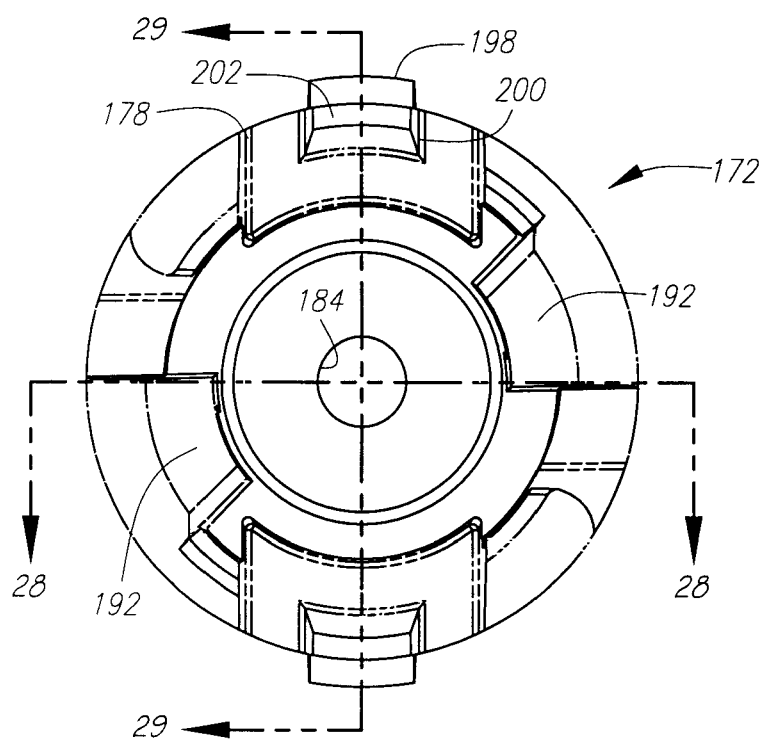
FIG. 27 is a top view of the luer hub assembly.
Figure 28:
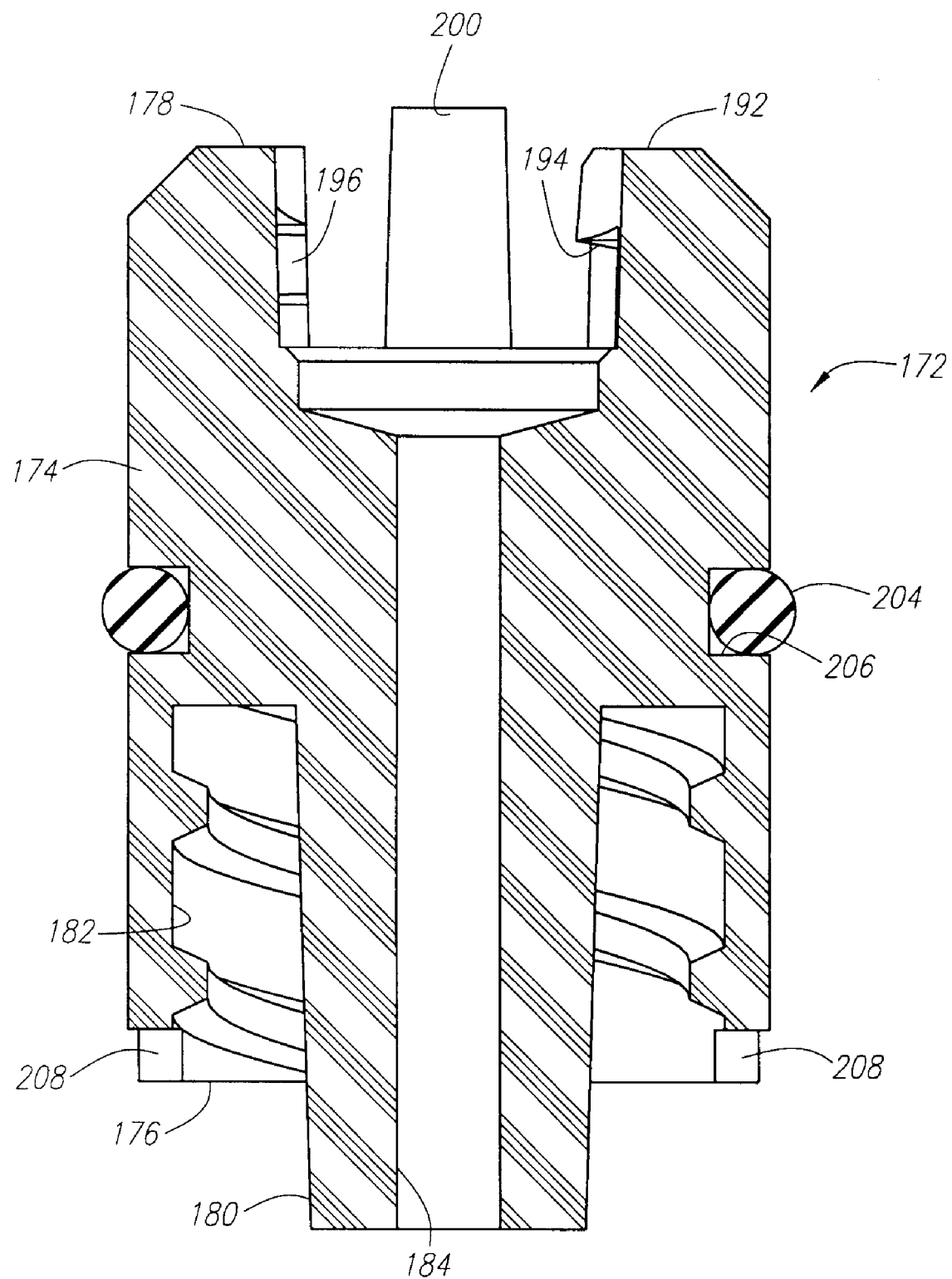
FIG. 28 is a cross-sectional view taken along line 28—28 of FIG. 27.
Figure 29:
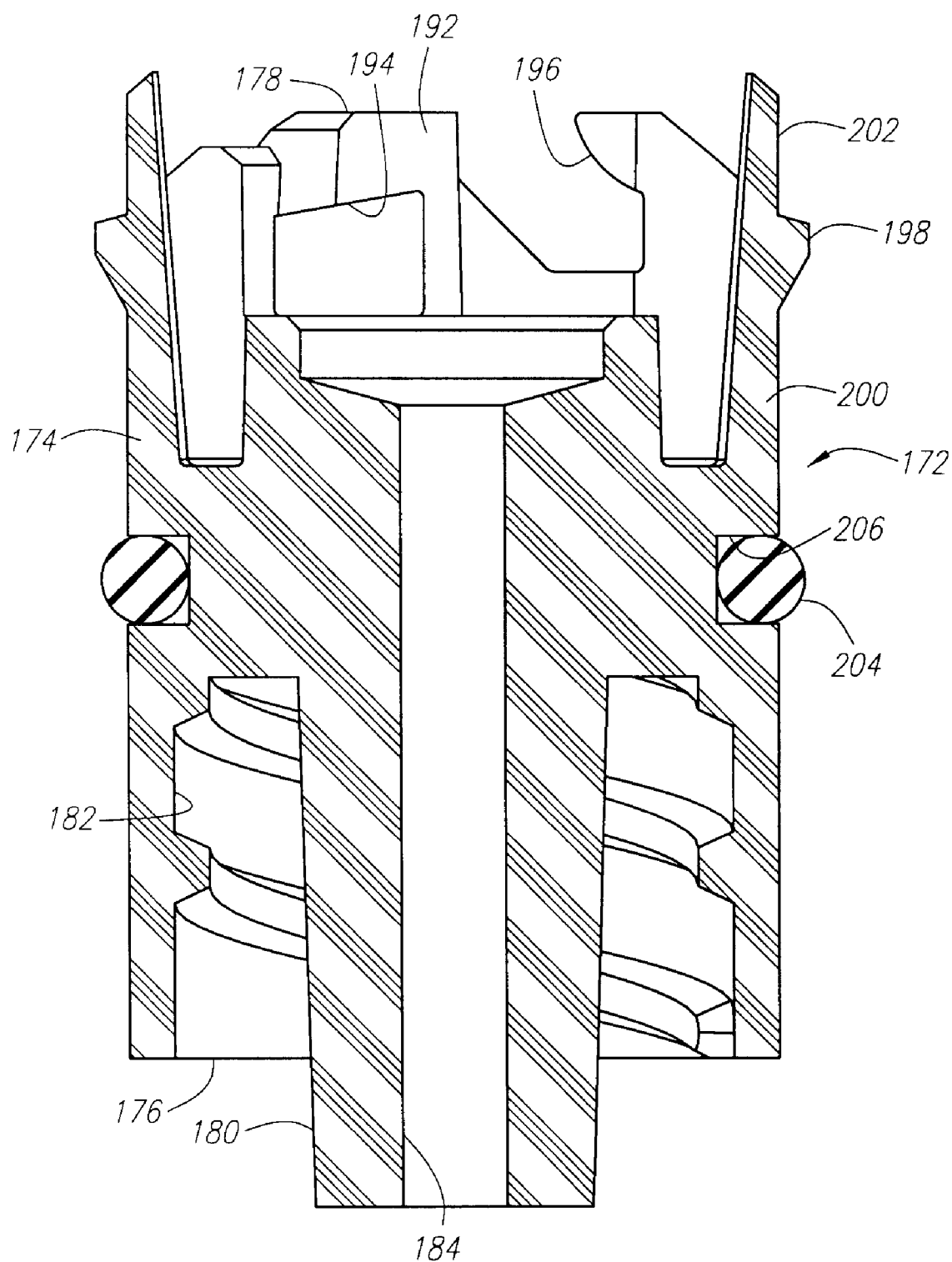
FIG. 29 is a cross-sectional view taken along line 29—29 of FIG. 27.
Figure 30:
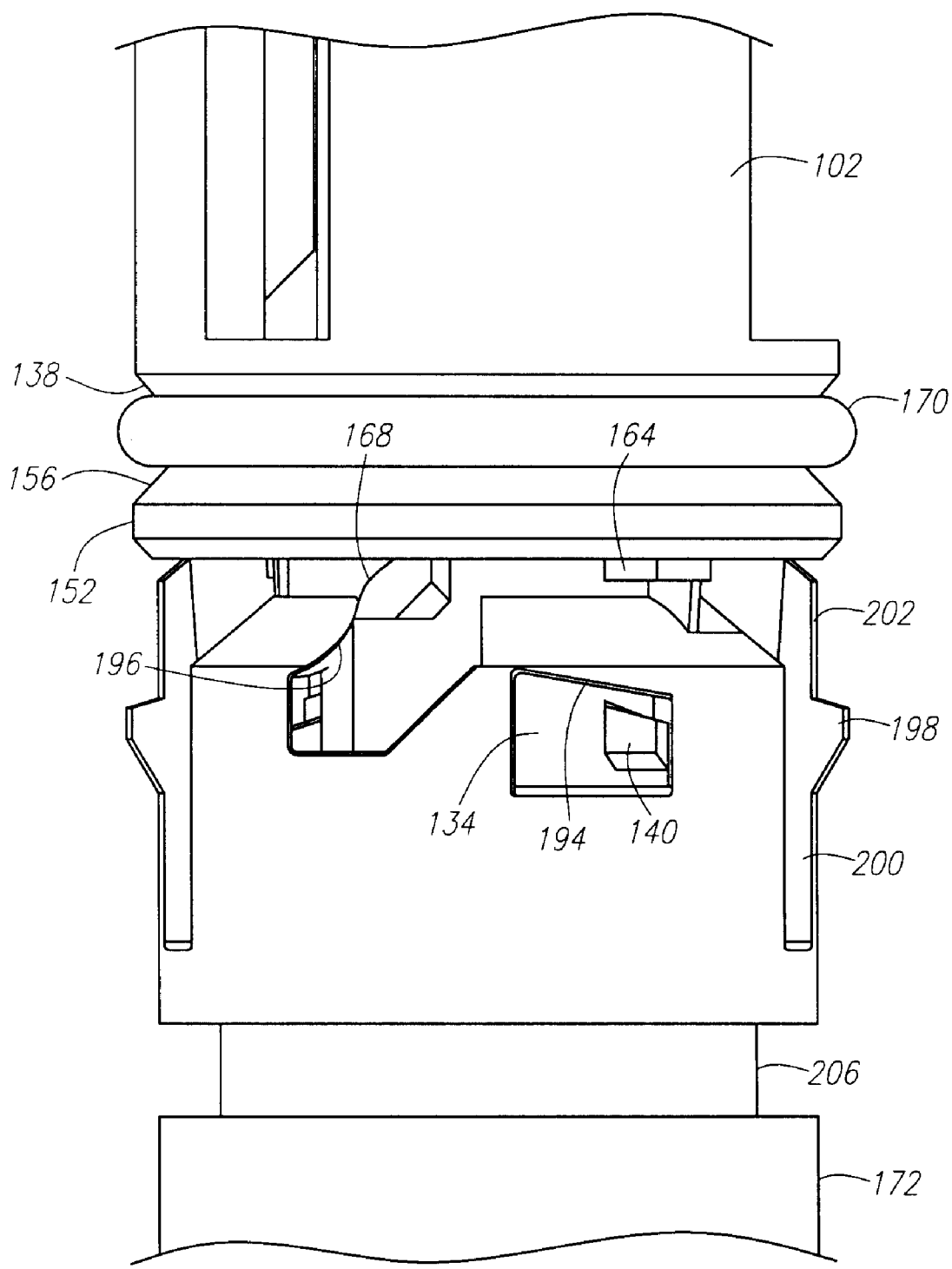
FIG. 30 is a partial side view of a seal stop and luer hub assembly in a first position.

A conical seal stop 152, illustrated in FIGS. 23 through 25, includes a central bore 154 to receive the probe 134 and is surrounded by a truncated conical surface 156. The truncated conical surface 156 is able to extend into and mate with the truncated conical surface of the cavity 136 on the seal end 112 of the inner plunger 102. A number of engagement means are provided on the seal stop 152.

Slots 158 extend outwardly from the central bore 154 to define inwardly and axially extending shoulders 160. The slots 158 loosely receive the lugs 150 such that axial rotation of the probe 134 relative to the seal stop 152 can occur.

At least a portion of the surface at diametrically opposed locations on the side of the seal stop 152 facing away from the seal end 112 of the inner plunger 102 forms two inwardly facing cam surfaces 162. These surfaces are inclined inwardly from the outer rim of the seal stop 152.

Resiliently mounted bayonet pins 164 extend inwardly from diametrically opposed positions. These bayonet pins 164, in cooperation with the bayonet slots 142 located on the probe 134, define an axially releasable engagement. The resilience of the mounts 165 for the pins 164 allows the pins 164 to move outwardly to surmount the ridges 148 in the bayonet slots 142. Thus, under a torque load, the probe 134 is able to rotate relative to the seal stop 152 to move the bayonet pins 164 from the axially engaged position in the circumferential grooves 144 to an axially disengaged position in the axial grooves 146. The relative motion between the probe 134 and the slots 158 is allowed by the slots 158 being wider than the lugs 150 and angularly arranged such that the inwardly and axially extending shoulders 160 do not engage the outwardly and axially extending shoulders of the lugs 150 until the bayonet pins 164 have moved over the ridges 148 to the axial extending grooves 146 of the bayonet slots 142.

Lastly, two support elements 166 extend axially from the conical seal stop 152 away from the seal end 112 of the inner plunger 102. These supports 166 include first engagement surfaces 168 which are inclined relative to the axis of the seal stop 152 and face the seal stop 152.

An annular seal 170, seen in FIGS. 30 through 33 typically provided by an O-ring, is positioned between the seal end 112 of the inner plunger 102 and the seal stop 152. With the seal stop 152 in mating engagement with the seal end 112, the external truncated conical surface 138 and the truncated conical surface 156 together provide a groove to hold the annular seal 170. The seal is in tension and forced radially outwardly into engagement with the interior sidewall of the barrel 22. With release of the seal stop 152 from the axially releasable engagement, the annular seal 170 retracts away from the external sidewall of the barrel 22. This release allows the plunger assembly to be retracted axially from the barrel 22 without significant sliding friction.

A luer hub assembly illustrated in FIGS. 26 through 29, generally designated 172, is located at the needle opening 26 of the barrel 22 and has a substantially cylindrical body 174 with a needle end 176 and an engagement end 178. At the needle end 176, a conical luer hub 180 centrally extends from the body 174. An internally threaded socket 182 surrounds the conical luer hub 180 and a passage 184 extends therethrough. The internally threaded socket 182 cooperates with the conical luer hub 180 to receive and retain a needle 186 having a standard conical sleeve 188 to fit over the conical luer hub 180. Lugs 190 on the periphery of the sleeve 188 engage the threads of the internally threaded socket 182 to positively retain the needle 186 in position.

The engagement end 178 of the luer hub assembly 172 includes a plurality of operative components. A retainer 192 extends from the engagement end 178 to define a retainer surface 194 which faces the body 174 of the luer hub assembly 172. The retainer surface 194 engages the retainer lugs 140 of the probe 134. With the plunger assembly fully extending into the barrel 22, the retainer lugs 140 and the retainer surfaces 194 are axially aligned but displaced from one another with the retainer lugs 140 closer to the needle opening 26 of the barrel 22 than are the retainer surfaces 194. This displacement allows the inner plunger assembly 102 to begin to retract before the retainer lugs 140 axially contact the retainer surfaces 194. This withdrawal of the inner piston assembly 102 draws a vacuum between the seal end 112 of the plunger 102 and the luer hub assembly 172. The vacuum in turn draws remaining liquid from the needle 186 into the syringe barrel 22.

Also located on the engagement end 178 of the luer hub assembly 172 is a pair of second engagement surfaces 196. The surfaces 196 engage the first engagement surfaces 168 of the seal stop 152. These surfaces 168 and 196 are steeply inclined and require greater force to engage than the retainer lugs 140 and retainer surfaces 194 which do not come into contact during the rotational engagement. This engagement of the surfaces 168 and 196 also requires more torque than the disengagement of the axially releasable engagement between the probe 134 and the seal stop 152 defined by the bayonet slots 142 and bayonet pins 164. Thus, the probe 134 and luer hub assembly 172 are insured to be engaged and the seal stop 152 and the probe 134 are assured to be disengaged prior to full engagement between the first engagement surfaces 168 and the second engagement surfaces 196. The second engagement surfaces 196 face toward the body 174 such that continued engagement between the surfaces 168 and 196 draws the seal stop 152 toward and into a locked position with the luer hub assembly 172.

The luer hub assembly 172 further includes resiliently mounted latch pins 198 radially extending from resilient supports 200. The latch pins 198 include cam followers 202 which extend axially toward the seal stop 152. The cam followers 202 are engaged by the inwardly facing cam surfaces 162. As the seal stop 152 is drawn toward the luer hub assembly 172 by the engagement surfaces 168 and 196, the inwardly facing cam surfaces force the cam followers 202 inwardly. This motion in turn moves the latch pins 198 inwardly. The latch pins are arranged to be positioned in the internal stops 54. Consequently, the luer hub assembly 172 is released by this motion of the latch pins 198.

A second annular seal 204 is arranged in a seal groove 206 about the body 174 of the luer hub assembly 172. The seal 204 is preferably an O-ring seal. As noted above, the internal sidewall portion 60 is tapered. Thus, as the luer hub assembly 172 moves away from the needle opening 26 of the barrel 22, the seal 204 is released from the wall.

Finally, the luer hub assembly 172 includes notches 208 which receive the luer hub stops 58 located at the needle opening 26 of the barrel 22. Thus, the luer hub assembly 172 is retained from any rotation until it is drawn into the barrel 22 and also is prevented from moving from the interior of the barrel 22 through the needle opening 26.

Turning to the operation of the hypodermic syringe, the syringe comes packaged with a sterile needle 186 engaged with the luer hub assembly 172 and extending from the barrel 22. The plunger cap 90 is positioned on the cap end 64 of the hollow outer plunger 62 with the resiliently mounted locks 86 extending into the tracks 98. The outer plunger 62 is substantially fully inserted into the barrel 22 such that the locking end 66 is adjacent to the second inward transition portion 42. The inner plunger assembly 102 is contracted into the interior of the hollow outer plunger 62. Thus, the radially extending stop 132 is fixed between the plunger stop 36 and the transition portion 30 of the barrel 22. The luer hub assembly 172 is located at the needle opening 26 of the barrel 22 with the notches 208 located in the luer hub stops 58 and the latch pins 198 locked in the internal stops 54. The seal stop 152 is engaged by the axially releasable engagement into mating relationship with the seal end 112 of the inner plunger assembly 102. With the seal stop 152 in this mating position, the annular seal 170 is radially expanded into sealed engagement with the internal surface of the barrel 22. The pins 128, 130 and the radially extending stop 132 are engaged with the grooves 68 and 70. With the bayonet pins 164 engaged in the bayonet slots 142, the lugs 150 of the probe 134 are displaced from the inwardly and axially extending shoulders 160 of the slots 158. The plunger assembly is indexed with the barrel by the plunger guide 44 within the longitudinal indexing groove 72 such that the retainer lugs 140 are angularly disengaged from the retainer surfaces 194 of the luer hub assembly 172.

To employ the syringe, the plunger assembly is extended. To do so, the outer plunger 62 is drawn from the barrel 22. This is accomplished by gripping the plunger cap 90 and pulling axially outwardly of the barrel 22. The outer plunger can be pulled outwardly until the sockets 78 move over the radially extending resiliently mounted guide pins 128, 130 with each become locked behind a catch 80. The inner plunger assembly 102 was restrained from moving outwardly with the outer plunger 62 by interference of the plunger stop 36 on the barrel 22 with the radially extending stop 132 on the inner plunger assembly 102. As the inner and outer plunger assemblies 102, 62 reach full extension, the ramp 71 on the stop groove 70 engages the release ramp 133 on the stop 132, releasing the stop 132 from the plunger stop 36. By not releasing the stop 132 before engagement of the guide pins 128, 130 with the sockets 78, the inner plunger assembly cannot be advanced into the barrel 22 before the plunger assembly is fully extended and locked. The stop 132 remains in the released position until the plunger assembly is again contracted. The force exerted against the plunger cap 90 to withdraw the outer plunger assembly is transmitted to the outer plunger 62 through the helical cam grooves 100 engaging the follower pins 84. This motion also stretches the resilient tension element.

With the plunger assembly extended, the thumb button 92 is depressed to advance the plunger assembly into the barrel, voiding the interior working volume. The plunger cap 90 may again be gripped and drawn outwardly to charge the working volume with a liquid to be injected or with a liquid to be withdrawn from a patient. The plunger assembly is able to move outwardly until the guide stop 76 meets the plunger guide 44. The liquid drawn into the working volume of the syringe may then be expelled by again advancing the retracted plunger assembly by pushing on the thumb button 92 of the plunger cap. Typically, the operator uses the thumb or first finger to depress the thumb button 92 while holding the syringe with two fingers about the finger grip 38 or a thumb and middle finger gripping the barrel. Once the liquid has been injected, the plunger assembly will be fully advanced in the barrel 22. At this point, illustrated in FIG. 30, only the plunger assembly has moved axially within the barrel 22 and only normal liquid injecting force has been applied.

After withdrawing the syringe from the point of injection, additional force is applied to the thumb button 92. The additional force drives the plunger cap 90 down into the first hollow portion 28 of the barrel 22. As the plunger cap 90 advances, the resiliently mounted locks 86 on the outer plunger 62 engage the longitudinally extending internal rails. The disengagement ramps 88 of the locks 86 encounter the ramps 34 of the rails 32 to force the locks 86 from the tracks 98. The rails 32 supplant the locks 86 in the tracks 98. At this point, the plunger cap 90 is no longer angularly indexed with the outer plunger 32. Rather, the plunger cap 90 is fixed from rotating relative to the barrel 22.

Figure 31:
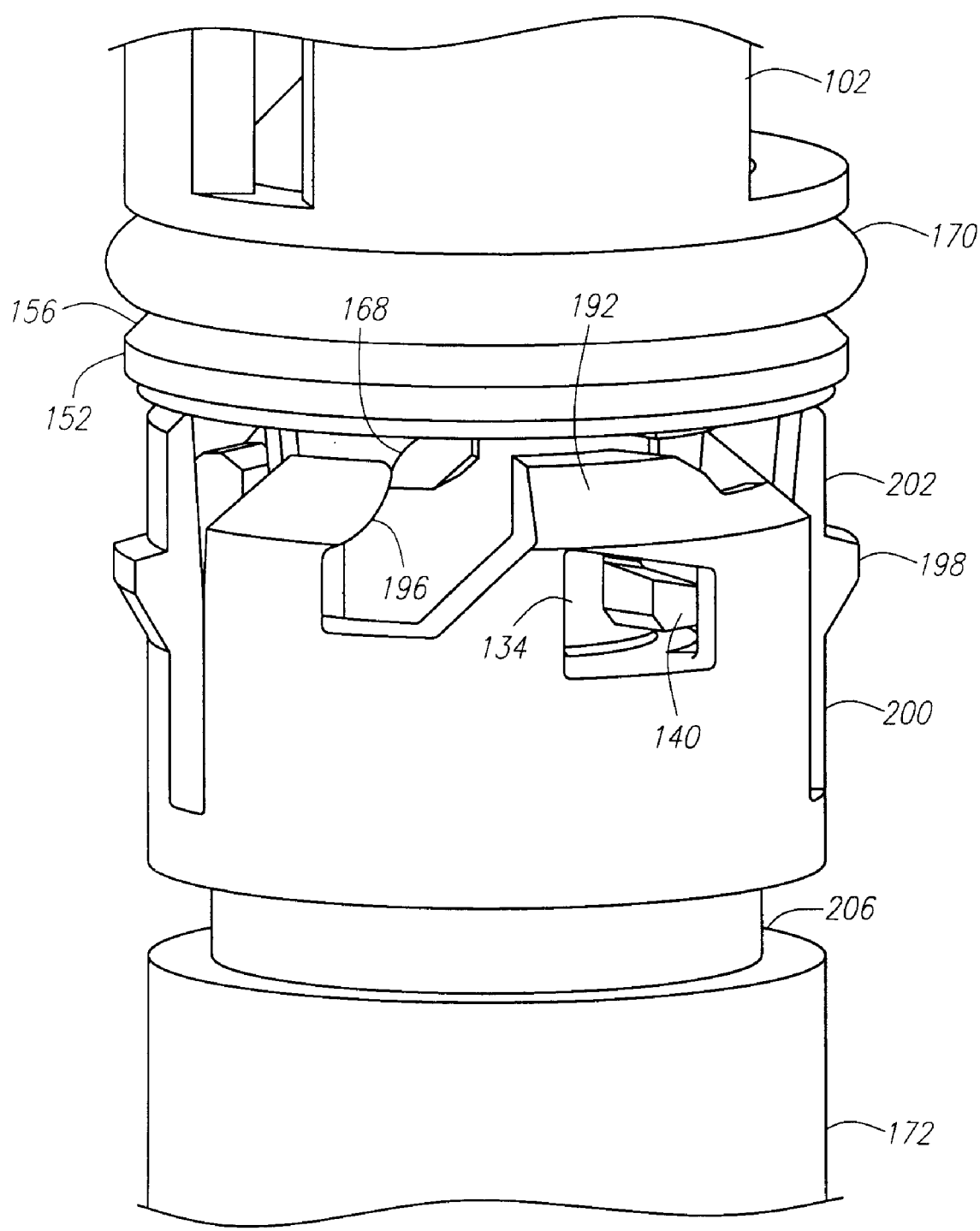
FIG. 31 is a perspective view of the seal stop and luer hub assembly in a second position.
Figure 32:
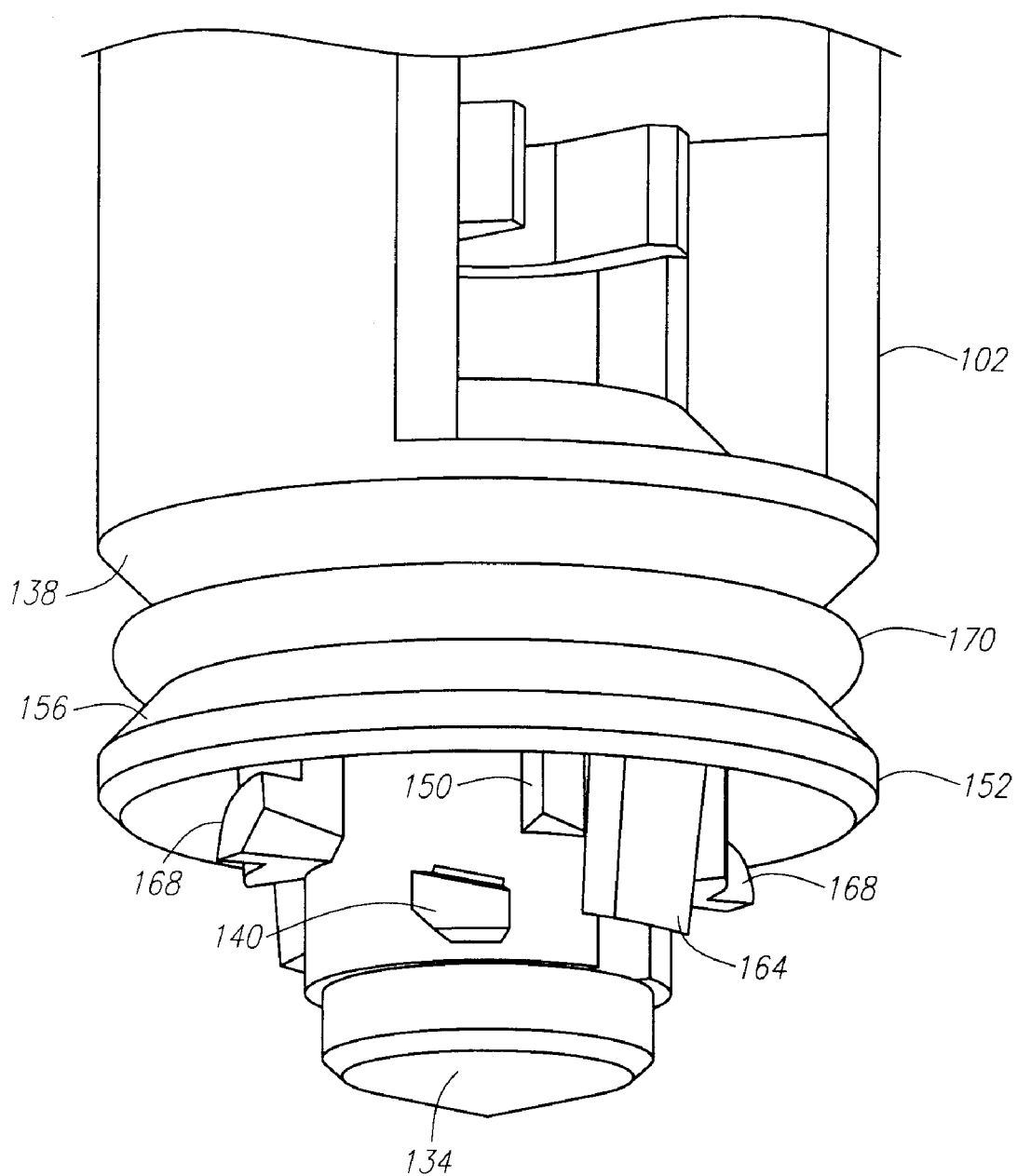
FIG. 32 is a perspective view of the seal stop and a probe.

As the plunger cap 90 further advances, the axial push is translated into rotational motion of the plunger assembly. The helical cam surfaces of the helical cam grooves 100 engage the follower pins 84 on the outer plunger 62 to develop torque within the outer plunger 62. As the outer plunger 62 is fully advanced within the barrel 22, the plunger guide 44 is aligned with the lateral release 74 of the longitudinal indexing groove. Thus, the plunger assembly is able to rotate without obstruction. As the plunger assembly rotates through a first angle, the retainer lugs 140 on the probe 134 rotate into displaced engagement with the retainer surface 194 on the luer hub assembly 172 as illustrated in FIG. 31. This first action insures that the luer hub assembly 172 is not left behind regardless of how the plunger assembly may retract under the influence of the stressed resilient tension element 120. As the retainer lugs 140 do not actually contact the retainer surfaces 194, no resistive force is encountered in this displaced engagement.

As the plunger cap 90 continues to be advanced, the probe 134 continues to rotate. The annular seal 170 is in friction engagement with the inner wall of the barrel 22. This frictional engagement may retain the seal stop 152 from rotating with the probe 134. Under this circumstance, the axially releasable engagement defined by the bayonet slots 142 and bayonet pins 164 will axially disengage prior to the engagement surfaces 168 of the seal stop 152 contacting the engagement surfaces 196 on the luer hub assembly 172. If instead, the seal stop 152 rotates with the plunger 134, the engagement surfaces 168 of the seal stop 152 initially engage the engagement surfaces 196 on the luer hub assembly 172. The axially releasable engagement is designed to resist disengagement with a first resistive torque that is substantially less than the resistive torque required to engage the first and second engagement surfaces 168 and 196. Consequently, the axially releasable engagement will disengage at that point. In either event, as illustrated (without the luer hub assembly 172) in FIG. 32, the conical seal stop 152 is released and the annular seal 170 retracts from the wall of the barrel 22. This is accomplished through a second angle of rotation between the probe 134 and the seal stop 152.

Figure 33:
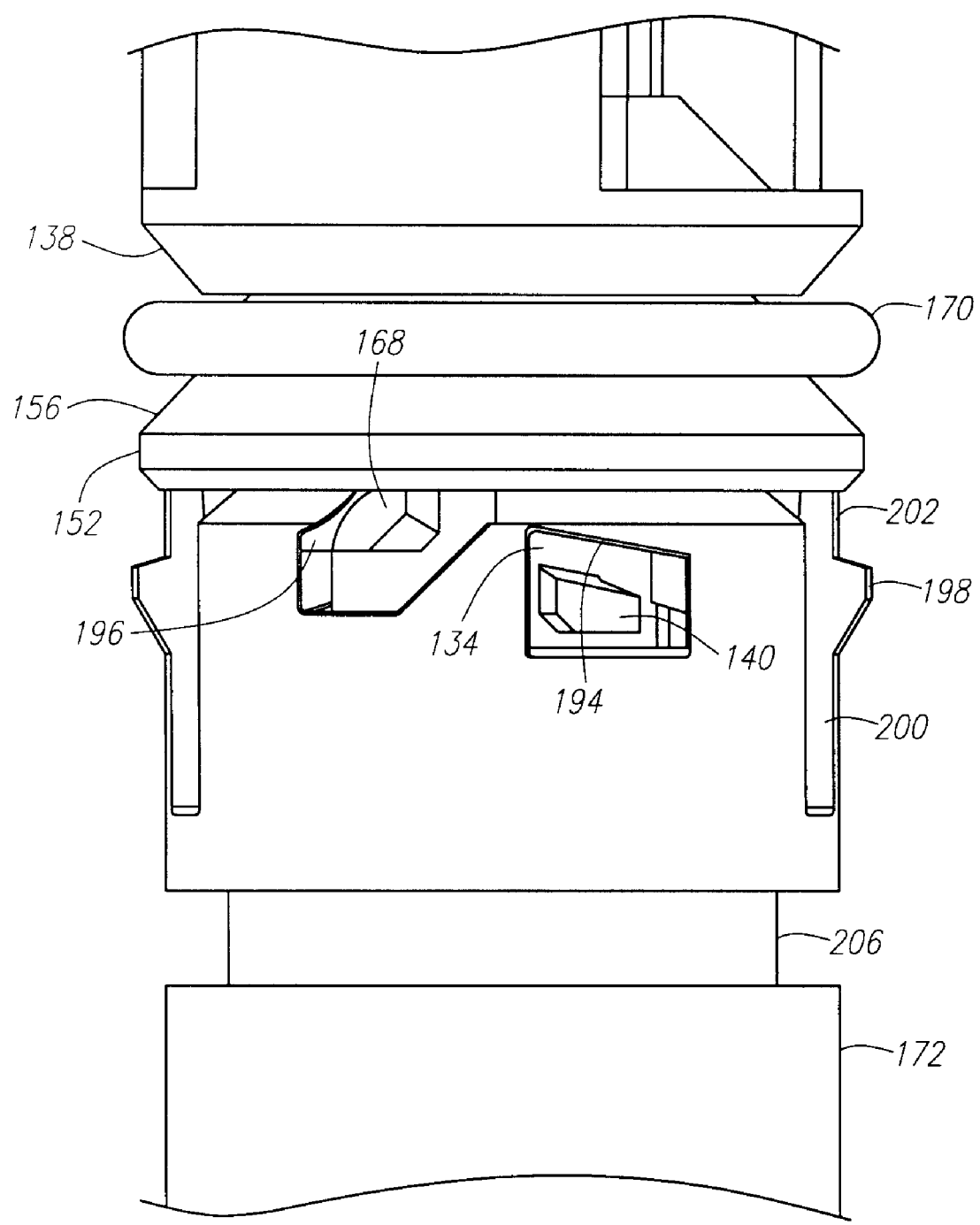
FIG. 33 is a side view of the seal stop and luer hub assembly in another position.

As the plunger cap 90 continues to be advanced, the lug 150 of the probe 134 engages the shoulders 160 of the slots 158. Further rotation of the plunger assembly results in the engagement surfaces 168 and 196 continuing into full engagement as illustrated in FIG. 33. This draws the seal stop 152 toward the luer hub assembly 172 to release the latch pins 198 as described above. This event occurs through an angle of rotation of the plunger assembly which is greater than that required to engage the retainer lugs with the retainer surfaces and greater than that required to release the annular seal 170.

Concurrently with the disengagement of the latch pins 198, the sockets 78 are moving into registry with the release elements 46 which are pushing the pins 128, 130 from the sockets 78. This rotational position is also greater than the angles necessary to engage the retainer lugs with the retainer surfaces and disengage the seal stop 152 from the seal end 112 of the inner plunger 102. When both the latch pins 198 and the radially extending resiliently mounted guide pins 128, 130 have been released, needle retraction is initiated.

Retraction of the needle 186 is initiated with the resilient tension element 120 tensioned to the maximum extent. The pins 128 and 130 are released from the slots 78. The latch pins 198 are released from the internal stops 54 and the annular seal 170 is retracted from the sidewall of the barrel 22. The second annular seal 204 remains in sealed engagement with the sidewall of the barrel 22 as retraction begins. Thus, some resistance is initially enountered. First the plunger assembly retracts until the retainer lugs 140 contact the retainer surfaces 194. As noted above, a vacuum is drawn on the needle to withdraw liquid therefrom. With the resilient tension elements 120 extended to substantially its maximum extent, the greatest force is available to draw the luer hub assembly 172 with the engaged seal 204 into the barrel 22. The seal 204 is against the portion of the wall 60 which is inwardly tapered toward the needle opening 26. Consequently, the resistive force of the frictional engagement of the seal 204 is reduced as the luer hub assembly 172 is drawn into the barrel 22. Thus, initial acceleration is less, due to the resistive frictional force of the seal 204. This further aids in preventing the release of liquids from the needle. The proportions of the various components are such that with full contraction of the resilient tension element 120, the tip of the needle has been drawn into the barrel 22 and is no longer a threat as a potential sharps injury.

Thus, an improved hypodermic syringe and a process for needle retraction are disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A hypodermic syringe comprising
a barrel;
a plunger assembly slidably extending into the barrel and including
a hollow outer plunger assembly having a first end, a second end and a first attachment at the first end facing the second end,
a hollow inner plunger assembly telescoping together with the outer plunger assembly and having an engagement end, a seal end and a second attachment facing the first attachment and located centrally of the hollow inner plunger assembly near the distal end, a resilient tension element fixed to the first attachment and the second attachment and being just substantially relaxed with the outer plunger assembly and the inner plunger assembly telescoped together, and a releasable engagement between the hollow outer plunger assembly and the hollow inner plunger assembly engageable with the hollow outer plunger assembly and the hollow inner plunger assembly telescoped to an extended position.

2. The hypodermic syringe of claim 1, the releasable engagement having a socket on the hollow outer plunger assembly near the second end and a resiliently mounted pin on the hollow inner plunger assembly near the engagement end engageable with the socket with the hollow outer plunger assembly and the hollow inner plunger assembly telescoped to an extended position.

3. The hypodermic syringe of claim 2, the barrel including a release element positioned to engage the resiliently mounted pin with movement of plunger assembly advanced fully in the barrel.

4. The hypodermic syringe of claim 3, the release element being an inwardly extending ramp, the socket having an open end angularly about the hollow outer plunger assembly to receive the ramp with rotation of the plunger assembly.

5. The hypodermic syringe of claim 4, the hollow outer plunger assembly further having a hollow outer plunger and a plunger cap at the first end extending over the hollow outer plunger, the cap having a cylindrical wall with a helical cam surface about a portion of the wall, the hollow outer plunger having a follower pin adjacent the first end engaged with the helical cam surface and slidable thereagainst.

6. The hypodermic syringe of claim 5, the barrel having a longitudinally extending internal rail, the wall having a track extending longitudinally of the barrel able to receive the internal rail, the hollow outer plunger further having a resiliently mounted lock near the first end engageable with the track and having a disengagement ramp, the internal rail extending against the disengagement ramp and displacing the lock from the track with near full insert of the plunger in the barrel.

7. The hypodermic syringe of claim 2, the hollow outer plunger assembly further having a longitudinally extending guide groove, the resiliently mounted pin being slidably engageable with the longitudinal guide groove with the hollow outer plunger assembly and the hollow inner plunger assembly telescoped less than to the extended position.

8. The hypodermic syringe of claim 1, the barrel having an inwardly extending plunger stop near the plunger opening, the hollow inner plunger assembly further having a radially extending stop near the engagement end engageable with the plunger stop with the engagement end near the plunger opening.

9. The hypodermic syringe of claim 1, the barrel including a plunger guide, the hollow outer plunger assembly further having a longitudinal indexing groove with two ends, the indexing groove slidably receiving the plunger guide and including a lateral release at one end of the indexing groove near the first end and a guide stop at the other end of the indexing groove near the second end, the guide stop limiting slidable movement of the plunger guide in the indexing groove.

10. The hypodermic syringe of claim 1 further comprising a luer hub assembly positioned in the barrel.

11. The hypodermic syringe of claim 1, the resilient tension element being a bungee.

12. A hypodermic syringe comprising a barrel having a longitudinally extending internal rail;

a plunger assembly slidably extending into the barrel and including a plunger having a first end and a second end and a plunger cap at the first end extending over the plunger, the plunger cap having a cylindrical wall with a helical cam surface about a portion of the wall and a track extending longitudinally of the barrel able to receive the internal rail, the plunger having a follower pin adjacent the first end engaged with the helical cam surface and slidable thereagainst and a resiliently mounted lock near the first end engageable with the track and having a disengagement ramp, the internal rail extending against the disengagement ramp and displacing the lock from the track with near full insert of the plunger in the barrel.

13. A hypodermic syringe comprising a barrel including a first opening at one end, a second opening at the other end and an internal sidewall;

a plunger assembly slidably extending into the barrel through the first opening and including a seal end having a cavity extending axially into the seal end and a probe extending axially from the cavity;

a seal stop positioned about the probe and positionable in mated relationship with the cavity;

an axially releasable engagement between the seal stop and the probe;

a first annular seal positioned between the seal stop and the seal end of the plunger assembly, the first annular seal being in sealed engagement with the internal sidewall with the seal stop held in mated engagement with the cavity by engagement of the axially releasable engagement and in disengagement with the internal sidewall with the axially releasable engagement in axial disengagement.

14. The hypodermic syringe of claim 13, the axially releasable engagement including a bayonet slot on the probe and a resiliently mounted bayonet pin on the seal stop.

15. The hypodermic syringe of claim 14, the bayonet pin being axially released from the bayonet slot by rotation of the seal stop relative to the probe.

16. The hypodermic syringe of claim 15, the barrel further including a longitudinally extending internal rail, the plunger assembly further including a plunger having a first end and a second end and a plunger cap at the first end extending over the plunger, the plunger cap having a cylindrical wall with a helical cam surface about a portion of the wall and a track extending longitudinally of the barrel able to receive the internal rail, the plunger having a follower pin adjacent the first end engaged with the helical cam surface and slidable thereagainst.

17. The hypodermic syringe of claim 13, the cavity having a truncated conical surface and the seal stop having a truncated conical surface to mate with the cavity.

18. The hypodermic syringe of claim 13, the plunger assembly further including a hollow outer plunger assembly having a first end, a second end and a first attachment at the first end facing the second end, a hollow inner plunger assembly telescoping together with the outer plunger assembly and having an engagement end, a seal end and a second attachment facing the first attachment and located centrally of the hollow inner plunger assembly near the distal end, a resilient tension element fixed to the first attachment and the second attachment and being just substantially relaxed with the hollow outer plunger assembly and the inner plunger assembly telescoped together, and a releasable engagement between the hollow outer plunger assembly and the hollow inner plunger assembly engageable with the hollow outer plunger assembly and the hollow inner plunger assembly telescoped to an extended position.

19. The hypodermic syringe of claim 18, the barrel further including a longitudinally extending internal rail, the hollow outer plunger assembly further including an outer plunger having a first end and a second end and a plunger cap at the first end extending over the outer plunger, the plunger cap having a cylindrical wall with a helical cam surface about a portion of the wall and a track extending longitudinally of the barrel able to receive the internal rail, the outer plunger having a follower pin adjacent the first end engaged with the helical cam surface and slidable thereagainst.

20. A hypodermic syringe comprising
a barrel including a first opening at one end, a second opening at the other end and an internal sidewall;
a plunger assembly slidably extending into the barrel through the first opening and including a seal end having a probe extending axially from the plunger assembly with a retainer lug;
a luer hub assembly positioned in the barrel at the second opening and including a body having a needle end, an engagement end, a luer hub at the needle end, a retainer surface facing the body near the engagement end engageable with the retainer lug through rotation of the plunger, the retainer surface and the retainer lug being axially displaced with the plunger assembly fully extended into the barrel with the retainer lug engaged with the retainer surface, the probe being rotatable through a first angle into displaced engagement with the retainer surface without resistive force between the retainer lug and the retainer surface.

21. A hypodermic syringe comprising
a barrel including a first opening at one end, a second opening at the other end and an internal sidewall;
a plunger assembly slidably extending into the barrel through the first opening and including a seal end having a probe extending axially from the plunger assembly with a retainer lug;
a luer hub assembly positioned in the barrel at the second opening and including a body having a needle end, an engagement end, a luer hub at the needle end, a retainer surface facing the body near the engagement end engageable with the retainer lug through rotation of the plunger, the barrel further including a longitudinally extending internal rail, the plunger assembly further including a plunger having a first end and a second end and a plunger cap at the first end extending over the plunger, the plunger cap having a cylindrical wall with a helical cam surface about a portion of the wall and a track extending longitudinally of the barrel able to receive the internal rail, the plunger having a follower pin adjacent the first end engaged with the helical cam surface and slidable thereagainst.

22. A hypodermic syringe comprising
a barrel including a first opening at one end, a second opening at the other end and an internal sidewall;
a plunger assembly slidably extending into the barrel through the first opening and including a seal end having a probe extending axially from the plunger assembly with a retainer lug;
a luer hub assembly positioned in the barrel at the second opening and including a body having a needle end, an engagement end, a luer hub at the needle end, a retainer surface facing the body near the engagement end engageable with the retainer a lug through rotation of the plunger, the internal sidewall including a portion inwardly tapered toward the second opening and the luer hub assembly further including an annular seal about the body between the body and the portion inwardly tapered.

23. A hypodermic syringe comprising
a barrel including a first opening at one end, a second opening at the other end and an internal sidewall;
a plunger assembly slidably extending into the barrel through the first opening and including a seal end and a probe extending axially from the seal end of the plunger;
a luer hub assembly positioned in the barrel at the second opening and including a body having a needle end, an engagement end, a luer hub at the needle end;
a seal stop positioned about the probe and positionable in mated relationship with the seal end;
an axially releasable engagement between the seal stop and the probe.

24. The hypodermic syringe of claim 23, the seal end further having a truncated conical cavity, the seal stop having a truncated conical surface to mate with the truncated conical cavity.

25. The hypodermic syringe of claim 24 further comprising
a first annular seal positioned between the seal stop and the seal end of the plunger assembly, the first annular seal being in sealed engagement with the internal sidewall with the seal stop held in mated engagement with the cavity by engagement of the axially releasable engagement and in disengagement with the internal sidewall with the axially releasable engagement in axial disengagement.

26. The hypodermic syringe of claim 23 further comprising
a first annular seal positioned between the seal stop and the seal end of the plunger assembly, the first annular seal being in sealed engagement with the internal sidewall with the seal stop held in mated engagement with the cavity by engagement of the axially releasable engagement and in disengagement with the internal sidewall with the axially releasable engagement in axial disengagement, the internal sidewall including a portion inwardly tapered toward the second opening and the luer hub assembly further including a second annular seal about the body between the body and the portion inwardly tapered.

27. The hypodermic syringe of claim 26, the probe having a retainer lug, the luer hub assembly further including a retainer surface in the body near the engagement end engageable with the retainer lug through rotation of the plunger, the retainer surface and the retainer lug being axially displaced with the plunger assembly fully extended into the barrel with the retainer lug engaged with the retainer surface.

28. The hypodermic syringe of claim 27, the probe being rotatable through a first angle into displaced engagement with the retainer surface without resistive force between the retainer lug and the retainer surface.

29. The hypodermic syringe of claim 23, the internal sidewall including a portion inwardly tapered toward the second opening and the luer hub assembly further including a second annular seal about the body between the body and the portion inwardly tapered.

30. The hypodermic syringe of claim 23 the luer hub assembly further including an internally threaded socket with the luer hub concentrically extending therethrough at the needle end.

31. The hypodermic syringe of claim 23, the axially releasable engagement including a bayonet slot on the probe and a resiliently mounted bayonet pin on the seal stop.

32. The hypodermic syringe of claim 23, the plunger assembly further including a hollow outer plunger assembly having a first end, a second end and a first attachment at the first end facing the second end, a hollow inner plunger assembly telescoping together with the outer plunger assembly and having an engagement end, a seal end and a second attachment facing the first attachment and located centrally of the hollow inner plunger assembly near the distal end, a resilient tension element fixed to the first attachment and the second attachment and being just substantially relaxed with the hollow outer plunger assembly and the inner plunger assembly telescoped together, and a releasable engagement between the hollow outer plunger assembly and the hollow inner plunger assembly engageable with the hollow outer plunger assembly and the hollow inner plunger assembly telescoped to an extended position.

33. The hypodermic syringe of claim 32, the barrel further including a longitudinally extending internal rail, the hollow outer plunger assembly further including an outer plunger having a first end and a second end and a plunger cap at the first end extending over the outer plunger, the plunger cap having a cylindrical wall with a helical cam surface about a portion of the wall and a track extending longitudinally of the barrel able to receive the internal rail, the outer plunger having a follower pin adjacent the first end engaged with the helical cam surface and slidable thereagainst.

34. A hypodermic syringe comprising
   a barrel including a first opening at one end, a second opening at the other end, an internal sidewall and an internal stop in the internal sidewall near the second opening;
   a plunger assembly slidably extending into the barrel through the first opening and including a seal end and a probe extending axially from the seal end of the plunger;
   a luer hub assembly positioned in the barrel at the second opening and including a body having a needle end, an engagement end, a luer hub at the needle end and a resiliently mounted latch pin near the engagement end extending radially outwardly of the luer hub assembly and engageable with the internal stop, the resiliently mounted latch pin having a cam follower;
   a seal stop positioned about the probe and positionable in mated relationship with the seal end, the seal stop having an inwardly facing cam surface, the resiliently mounted latch pin being engageable with the inwardly facing cam surface;
   an axially releasable engagement between the seal stop and the probe.

35. The hypodermic syringe of claim 34, the seal stop further having a support extending from the seal stop toward the luer hub assembly with a first engagement surface facing the seal stop, the luer hub assembly further including a second engagement surface facing the body and engageable with the first engagement surface through rotation of the probe with the plunger fully extended into the barrel, the first and second engagement surfaces drawing the seal stop and the luer hub assembly toward one another with further rotation of the seal stop relative to the luer hub assembly.

36. The hypodermic syringe of claim 35, the probe having an outwardly and axially extending shoulder and the seal stop further having an inwardly and axially extending shoulder receiving the outwardly and axially extending shoulder through rotation of the probe relative to the seal stop.

37. The hypodermic syringe of claim 36, the probe further having a retainer lug, the luer hub assembly further including a retainer surface in the body near the engagement end engageable with the retainer lug through rotation of the plunger, the probe being rotatable through a first angle relative to the hub assembly into displaced engagement of the retainer lug with the retainer surface without resistive force between the retainer lug and the retainer surface, the probe being rotatable through a second angle relative to the seal stop with the inwardly and axially extending shoulder moving toward the outwardly and axially extending shoulder to axially disengage the axially releasable engagement with a first resistive torque, the probe being rotatable through a third angle relative to the luer hub assembly to engage the first engagement surface and the second engagement surface with engagement of the inwardly facing cam surface and the cam follower, releasing the latch pin from the internal stop, with a second resistive torque greater than the first resistive torque.

38. The hypodermic syringe of claim 37, the plunger assembly further including a hollow outer plunger assembly having a first end, a second end and a first attachment at the first end facing the second end, a hollow inner plunger assembly telescoping together with the outer plunger assembly and having an engagement end, a seal end and a second attachment facing the first attachment and located centrally of the hollow inner plunger assembly near the distal end, a resilient tension element fixed to the first attachment and the second attachment and being just substantially relaxed with the hollow outer plunger assembly and the inner plunger assembly telescoped together, and a releasable engagement between the hollow outer plunger assembly and the hollow inner plunger assembly engageable with the hollow outer plunger assembly and the hollow inner plunger assembly telescoped to an extended position.

39. The hypodermic syringe of claim 38, the releasable engagement having a socket on the hollow outer plunger assembly near the second end and a resiliently mounted pin on the hollow inner plunger assembly near the engagement end engageable with the socket with the hollow outer plunger assembly and the hollow inner plunger assembly telescoped to an extended position, the barrel including a release element positioned to engage the resiliently mounted pin with rotation of plunger assembly advanced fully in the barrel.

40. The hypodermic syringe of claim 39, the plunger assembly being rotatable through a fourth angle relative to the barrel greater than the first angle and greater than the second angle to engage the release element with the resiliently mounted pin to disengage the releasable engagement.

41. The hypodermic syringe of claim 40, the barrel further including a longitudinally extending internal rail, the hollow outer plunger assembly further including an outer plunger having a first end and a second end and a plunger cap at the first end extending over the outer plunger, the plunger cap having a cylindrical wall with a helical cam surface about a portion of the wall and a track extending longitudinally of the barrel able to receive the internal rail, the outer plunger having a follower pin adjacent the first end engaged with the helical cam surface and slidable thereagainst.

42. The hypodermic syringe of claim 34, the internal sidewall including a portion inwardly tapered toward the second opening and the luer hub assembly further including a second annular seal about the body between the body and the portion inwardly tapered.

43. The hypodermic syringe of claim 34 the luer hub assembly further including an internally threaded socket with the luer hub concentrically extending therethrough at the needle end.

44. The hypodermic syringe of claim 34, the axially releasable engagement including a bayonet slot on the probe and a resiliently mounted bayonet pin on the seal stop.

45. The hypodermic syringe of claim 34, the plunger assembly further including a hollow outer plunger assembly having a first end, a second end and a first attachment at the first end facing the second end, a hollow inner plunger assembly telescoping together with the outer plunger assembly and having an engagement end, a seal end and a second attachment facing the first attachment and located centrally of the hollow inner plunger assembly near the distal end, a resilient tension element fixed to the first attachment and the second attachment and being just substantially relaxed with the hollow outer plunger assembly and the inner plunger assembly telescoped together, and a releasable engagement between the hollow outer plunger assembly and the hollow inner plunger assembly engageable with the hollow outer plunger assembly and the hollow inner plunger assembly telescoped to an extended position.

46. The hypodermic syringe of claim 45, the barrel further including a longitudinally extending internal rail, the hollow outer plunger assembly further including an outer plunger having a first end and a second end and a plunger cap at the first end extending over the outer plunger, the plunger cap having a cylindrical wall with a helical cam surface about a portion of the wall and a track extending longitudinally of the barrel able to receive the internal rail, the outer plunger having a follower pin adjacent the first end engaged with the helical cam surface and slidable thereagainst.

47. A hypodermic syringe retraction method comprising
extending a plunger assembly and a resilient tension element within a barrel, the plunger assembly having an outer plunger and an inner plunger telescoping together with the outer plunger and the resilient tension element being fixed at the ends to the outer plunger and the inner plunger, by drawing the outer plunger outwardly from the barrel and engaging the outer plunger and the inner plunger together when telescoped to an extended position;
advancing the extended plunger assembly within the barrel to a luer hub;
drawing liquid into the barrel by retracting the extended and advanced plunger assembly;
expelling the liquid drawn by advancing the retracted plunger assembly;
engaging the luer hub assembly with the plunger assembly;
releasing the engagement between the outer plunger and the inner plunger.

48. The hypodermic syringe retraction method of claim 47, engaging the luer hub assembly with the plunger assembly including advancing the plunger assembly fully within the barrel and rotating a retainer lug on the seal end of the plunger assembly into spaced engagement with a retainer surface on the luer hub assembly.

49. The hypodermic syringe retraction method of claim 48, rotating the retainer lug on the seal end of the plunger assembly including axially pushing on a cap of the plunger assembly on the end of the plunger extending from the barrel and translating the axial push to rotation of the plunger assembly.

50. The hypodermic syringe retraction method of claim 49, translating the axial push to rotation of the plunger assembly including releasing a resiliently mounted lock on the outer plunger from the cap, engaging a rail on the barrel with the cap, engaging a helical cam surface on the cap with a follower pin on the outer plunger while axially pushing on the cap.

51. The hypodermic syringe retraction method of claim 47, releasing the engagement between the outer plunger and the inner plunger including advancing the plunger assembly fully within the barrel and rotating the plunger assembly through at least a first angle to engage the engagement with a release element on the internal sidewall of the barrel.

52. The hypodermic syringe retraction method of claim 51, engaging the luer hub assembly with the plunger assembly including advancing the plunger assembly fully within the barrel and rotating a retainer lug on the seal end of the plunger assembly through at least a second angle into spaced engagement with a retainer surface on the luer hub assembly, the rotation of the plunger assembly and the rotation of the probe being together with the second angle being smaller than the first angle.

53. The hypodermic syringe retraction method of claim 52, rotating the retainer lug on the seal end of the plunger assembly and rotating the plunger assembly including axially pushing on a cap of the plunger assembly on the end of the plunger extending from the barrel and translating the axial push to rotation of the plunger assembly.

54. The hypodermic syringe retraction method of claim 53, translating the axial push to rotation of the plunger assembly including releasing a resiliently mounted lock on the outer plunger from the cap, engaging a rail on the barrel with the cap, engaging a helical cam surface on the cap with a follower pin on the outer plunger while axially pushing on the cap.

55. A hypodermic syringe retraction method comprising
extending a plunger assembly having a seal stop releaseably engaged on a seal end thereof fully into a barrel;
radially retracting an annular seal held between the seal end of the plunger assembly and the seal stop including releasing the seal stop from the seal end of the plunger assembly;
engaging the seal stop with a luer hub assembly;
releasing the luer hub from the barrel including disengaging a latch pin on the luer hub assembly from an interior stop on the interior sidewall of the barrel.

56. The hypodermic syringe retraction method of claim 55, releasing the seal stop from the seal end of the plunger assembly including rotating the plunger in the barrel with the seal stop restricted from rotation by frictional engagement of the annular seal with the barrel through a first angle.

57. The hypodermic syringe retraction method of claim 56, engaging the seal stop with the luer hub assembly including rotating the seal stop assembly through a second angle by rotationally engaging the seal stop and the plunger after rotation of the plunger through the first angle, rotating the plunger with the seal stop through the second angle and engaging mating engagement surfaces on the seal stop and on the luer hub assembly.

58. The hypodermic syringe retraction method of claim 57, disengaging the latch pin on the luer hub assembly from an interior stop on the interior sidewall of the barrel including drawing an inwardly facing cam surface on the seal stop against a cam follower on the latch pin to move the latch pin inwardly from the interior stop by rotating the seal stop relative to the luer hub assembly with the mating engagement surfaces engaged.

59. The hypodermic syringe retraction method of claim 55, engaging the seal stop with the luer hub assembly including rotating the seal stop assembly through an angle by rotationally engaging the seal stop and the plunger, rotating the plunger with the seal stop through the angle and engaging mating engagement surfaces on the seal stop and on the luer hub assembly.

60. The hypodermic syringe retraction method of claim 59, disengaging the latch pin on the luer hub assembly from an interior stop on the interior sidewall of the barrel including drawing an inwardly facing cam surface on the seal stop against a cam follower on the latch pin to move the latch pin inwardly from the interior stop by rotating the seal stop relative to the luer hub assembly with the mating engagement surfaces engaged.

61. A hypodermic syringe retraction method comprising
    extending a plunger assembly and a resilient tension element within a barrel, the plunger assembly having an outer plunger and an inner plunger telescoping together with the outer plunger and the resilient tension element being fixed at the ends to the outer plunger and the inner plunger, by drawing the outer plunger outwardly from the barrel and engaging the outer plunger and the inner plunger together when telescoped to an extended position;
    advancing the extended plunger assembly within the barrel to a luer hub;
    drawing liquid into the barrel by retracting the extended and advanced plunger assembly;
    expelling the liquid drawn by advancing the retracted plunger assembly;
    extending a plunger assembly having a seal stop releaseably engaged on the seal end thereof fully into a barrel;
    engaging the luer hub assembly with the plunger assembly;
    radially retracting an annular seal held between the seal end of the plunger assembly and the seal stop including releasing the seal stop from the seal end of the plunger assembly;
    engaging the seal stop with a luer hub assembly;
    releasing the engagement between the outer plunger and the inner plunger;
    releasing the luer hub from the barrel including disengaging a latch pin on the luer hub assembly from an interior stop on the interior sidewall of the barrel.

62. The hypodermic syringe retraction method of claim 61, engaging the luer hub assembly with the plunger assembly including advancing the plunger assembly fully within the barrel and rotating a retainer lug on the seal end of the plunger assembly into spaced engagement with a retainer surface on the luer hub assembly.

63. The hypodermic syringe retraction method of claim 62, rotating the retainer lug on the seal end of the plunger assembly including axially pushing on a cap of the plunger assembly on the end of the plunger extending from the barrel and translating the axial push to rotation of the plunger assembly.

64. The hypodermic syringe retraction method of claim 63, translating the axial push to rotation of the plunger assembly including releasing a resiliently mounted lock on the outer plunger from the cap, engaging a rail on the barrel with the cap, engaging a helical cam surface on the cap with a follower pin on the outer plunger while axially pushing on the cap.

65. The hypodermic syringe retraction method of claim 61, releasing the engagement between the outer plunger and the inner plunger including advancing the plunger assembly fully within the barrel and rotating the plunger assembly through at least a first angle to engage the engagement with a release element on the internal sidewall of the barrel.

66. The hypodermic syringe retraction method of claim 65, engaging the luer hub assembly with the plunger assembly including advancing the plunger assembly fully within the barrel and rotating a retainer lug on the seal end of the plunger assembly through at least a second angle into spaced engagement with a retainer surface on the luer hub assembly, the rotation of the plunger assembly and the rotation of the probe being together with the second angle being smaller than the first angle.

67. The hypodermic syringe retraction method of claim 66, rotating the retainer lug on the seal end of the plunger assembly and rotating the plunger assembly including axially pushing on a cap of the plunger assembly on the end of the plunger extending from the barrel and translating the axial push to rotation of the plunger assembly.

68. The hypodermic syringe retraction method of claim 67, translating the axial push to rotation of the plunger assembly including releasing a resiliently mounted lock on the outer plunger from the cap, engaging a rail on the barrel with the cap, engaging a helical cam surface on the cap with a follower pin on the outer plunger while axially pushing on the cap.

69. The hypodermic syringe retraction method of claim 61, releasing the seal stop from the seal end of the plunger assembly including rotating the plunger in the barrel with the seal stop restricted from rotation.

70. The hypodermic syringe retraction method of claim 69, engaging the seal stop with the luer hub assembly including rotating the seal stop assembly through a second angle by rotationally engaging the seal stop and the plunger after rotation of the plunger through the first angle, rotating the plunger with the seal stop through the second angle and engaging mating engagement surfaces on the seal stop and on the luer hub assembly.

71. The hypodermic syringe retraction method of claim 70, disengaging the latch pin on the luer hub assembly from an interior stop on the interior sidewall of the barrel including drawing an inwardly facing cam surface on the seal stop against a cam follower on the latch pin to move the latch pin inwardly from the interior stop by rotating the seal stop relative to the luer hub assembly with the mating engagement surfaces engaged.

72. The hypodermic syringe retraction method of claim 61, engaging the seal stop with the luer hub assembly including rotating the seal stop assembly through an angle by rotationally engaging the seal stop and the plunger, rotating the plunger with the seal stop through the angle and engaging mating engagement surfaces on the seal stop and on the luer hub assembly.

73. The hypodermic syringe retraction method of claim 72, disengaging the latch pin on the luer hub assembly from an interior stop on the interior sidewall of the barrel including drawing an inwardly facing cam surface on the seal stop against a cam follower on the latch pin to move the latch pin inwardly from the interior stop by rotating the seal stop relative to the luer hub assembly with the mating engagement surfaces engaged.

* * * * *